(12) United States Patent
White et al.

(10) Patent No.: US 9,730,629 B2
(45) Date of Patent: *Aug. 15, 2017

(54) VAGINAL BIOMECHANICS ANALYZER

(71) Applicant: BOARD OF REGENTS, THE UNIVERSITY OF TEXAS SYSTEM, Austin, TX (US)

(72) Inventors: Carter B. White, Mesquite, TX (US); Philippe Zimmern, Dallas, TX (US); Robert C. Eberhart, Dallas, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/210,383

(22) Filed: Jul. 14, 2016

(65) Prior Publication Data

US 2016/0317078 A1 Nov. 3, 2016

Related U.S. Application Data

(63) Continuation-in-part of application No. 14/600,656, filed on Jan. 20, 2015, which is a continuation-in-part of application No. 13/564,682, filed on Aug. 1, 2012.
(Continued)

(51) Int. Cl.
*A61B 5/103* (2006.01)
*A61B 5/117* (2016.01)
(Continued)

(52) U.S. Cl.
CPC .......... *A61B 5/4337* (2013.01); *A61B 5/0055* (2013.01); *A61B 5/442* (2013.01);
(Continued)

(58) Field of Classification Search
CPC ....... A61B 5/0055; A61B 5/441; A61B 5/442; A61B 5/4337
(Continued)

(56) References Cited

U.S. PATENT DOCUMENTS 5,278,776 A   1/1994  Fisher et al.
6,741,895 B1  5/2004  Garni et al.
(Continued)

FOREIGN PATENT DOCUMENTS

KR   20090101530 A   9/2009

*Primary Examiner* — Max Hindenburg
*Assistant Examiner* — Jonathan M Foreman
(74) *Attorney, Agent, or Firm* — Edwin S. Flores; Daniel J. Chalker; Chalker Flores, LLP

(57) ABSTRACT

The present invention includes a device and method for measuring skin elasticity that comprises: a probe with one or more holes, a vacuum source, a pressure sensor, and one or more infrared or optical proximity sensors aligned about the one or more holes, wherein the probe further comprises a raised area surrounding the one or more holes; and a processor for recording the deformation of the skin using a control unit comprising a microcontroller connected to the one or more infrared or optical proximity sensors and the one or more pressure sensors, to measure an amount of skin drawn into and out of the one or more holes to determine the distance between the one or more proximity sensors and the skin both inside and outside the probe.

12 Claims, 18 Drawing Sheets

Related U.S. Application Data

(60) Provisional application No. 61/574,290, filed on Aug. 1, 2011.

(51) Int. Cl.
*A61B 5/00* (2006.01)
*A61F 2/00* (2006.01)

(52) U.S. Cl.
CPC .......... *A61F 2/0063* (2013.01); *A61B 5/0082* (2013.01); *A61F 2250/0004* (2013.01)

(58) Field of Classification Search
USPC .................................. 600/38, 587, 588, 591
See application file for complete search history.

(56) References Cited

U.S. PATENT DOCUMENTS

| | | |
|---|---|---|
| 7,892,176 B2 | 2/2011 | Wodnicki et al. |
| 7,955,278 B1 | 6/2011 | Sarvazyan |
| 8,175,689 B2 | 5/2012 | Hunter-Jones et al. |
| 2005/0085827 A1 | 4/2005 | G. et al. |
| 2008/0077053 A1 | 3/2008 | Epstein et al. |
| 2011/0130683 A1* | 6/2011 | Sarvazyan ........... A61B 5/0055 600/587 |
| 2011/0230769 A1 | 9/2011 | Yamazaki |
| 2013/0035611 A1 | 2/2013 | White |
| 2013/0144191 A1* | 6/2013 | Egorov ................. A61B 5/227 600/591 |
| 2015/0133750 A1 | 5/2015 | White et al. |
| 2016/0106468 A1* | 4/2016 | Jansen ................... A61H 7/005 606/131 |

* cited by examiner

VAGINAL BIOMECHANICS ANALYZER

CROSS-REFERENCE TO RELATED APPLICATIONS

This application is a continuation-in-part of U.S. patent application Ser. No. 14/600,656, filed Jan. 20, 2015, which is a continuation-in-part of U.S. patent application Ser. No. 13/564,682, filed Aug. 1, 2012 which claims priority to U.S. Provisional Application Ser. No. 61/574,290, filed Aug. 1, 2011, the entire contents of which are incorporated herein by reference.

TECHNICAL FIELD OF THE INVENTION

The present invention relates in general to the field of biomechanical skin analyzers, and more particularly, to a novel biomechanical tissue analyzer.

STATEMENT OF FEDERALLY FUNDED RESEARCH

None.

BACKGROUND OF THE INVENTION

Without limiting the scope of the invention, its background is described in connection with pelvic organ prolapse.

The present invention relates to an electro mechanical device that measures skin elasticity for assessing the viscoelastic properties of the anterior wall of the vagina. Vaginal wall tissue deterioration can cause pelvic organ prolapse (POP), a hernia of the pelvic organs to or through the vaginal opening. POP affects a large number of aging women that often necessitates surgical repair and tends to recur over time. Approximately 200,000 operations are performed yearly in the United States for POP. Although not life threatening, POP is life altering and results in significant quality of life changes in women.

Medical researchers have studied vaginal wall properties in freshly excised tissue, at the time of surgery, using an Instron tensile testing machine but this is limited by its applicability, namely patients requiring surgery. Currently, evaluation of the vaginal wall is limited to physical examination and imaging modalities. There are no quantitative and practical devices that a physician can use during an office visit to measure the unique viscoelastic properties of the vagina to objectively determine tissue deterioration. The ability to measure the elasticity of the inner walls of the vagina in healthy patients for study controls, patients in less advanced degrees of POP, patients before and after surgical repair and patients on hormonal therapy will lead to a myriad of common vaginal interventions, from pelvic floor therapy to reconstructive surgery. Like the thermometer to objectively determine how sick a feverish patient is, the present invention will serve as a diagnostic resource for clinicians and researchers interested in the management of POP.

Skin elasticity measurement devices include US Patent Application Publication No. US 2008/0234607 A1. In this US patent application, the user applies a vacuum to a chamber that is placed over an area of the skin. When the vacuum draws the skin through an opening a video camera in an adjacent chamber captures light reflected from the skin.

U.S. Pat. No. 7,955,278 B1 creates a vacuum that draws the skin into a chamber until the skin reaches the vacuum tube in the chamber. The vacuum pressures are measured and pressure changes are used to calculate elasticity.

U.S. Pat. No. 5,278,776 describes the use of a camera that monitors the movement of dots placed on the skin. When the vacuum is applied the skin moves into the chamber causing the dots to move. The elasticity is determined by the dot separation.

SUMMARY OF THE INVENTION

The present invention is a safe, easily insertable, user-friendly, and quickly sterilizable vaginal device that would allow rapid and reproducible measurements of different areas of the vagina, in the office setting. The present invention is simple to use and extremely accurate. The probe design is small enough to be inserted in the vagina, yet precisely measure the tissue deflection and recovery under mild suction and vacuum release. The stored data for each patient can be compared to previously collected data to detect the changes in tissue elasticity. For the first time, the present invention allows for a direct in-vivo measurement of vaginal wall tissue properties.

In one embodiment, the present invention includes a device for measuring skin elasticity comprising: a probe, wherein the probe comprises one or more holes, a vacuum source, a pressure sensor, and one or more proximity sensors (e.g., infrared or optical) aligned about the one or more holes, wherein the probe further comprises a raised area surrounding the one or more holes; and a processor for recording the deformation of the skin using a control unit comprising a microcontroller connected to the one or more proximity sensors and the one or more pressure sensors, wherein the proximity sensor is positioned at a pre-determined distance from the skin, wherein a vacuum in the probe is capable of pulling skin into the one or more holes and the proximity sensor is capable of measuring an amount of skin drawn into and out of the one or more holes to determine the distance between the one or more proximity sensors and the skin before, during and after release of the vacuum, and wherein the processor calculates the skin elasticity of the inner walls of the skin based on the distance to the one or more proximity sensors throughout a measurement cycle both inside and outside the probe. In one aspect, the raised area surrounds the hole and further comprises a polished surface that provides improved contact with the skin during operation. In another aspect, the device further comprises a vacuum release line in fluid communication with the one or more holes of the probe to provide fresh air to refill the probe after a test under vacuum. In another aspect, the device further comprises an accelerometer or gyroscope that measures the relative angle of the probe between a vertical and horizontal position. In another aspect, the control unit further comprises a switch, an electronic control valve, and a liquid crystal display, and wherein a wand assembly is defined further as comprising a detachable handle and the probe, wherein the control unit records and stores a vacuum data and a proximity sensor data used to calculate the skin elasticity, and a memory connected to the processor to store data from the proximity sensor for immediate processing or processing at a later time. In another aspect, the proximity sensor comprises a camera capable of detecting an extent and a shape of skin deflection over time. In another aspect, the probe further comprises at least one orifice that comprises a membrane to determine the rheological properties of a liquid on or about the skin. In another aspect, the handle is further defined as comprising a circuit board, a proximity sensor, a data cable connection, and a vacuum tube connection, and the proximity sensor is mounted on a circuit board that is within the probe and is attached to the handle. In another aspect, the proximity sensor comprises an infrared or optical sensor capable of detecting an extent and a shape of skin deflection over time without contacting the skin being measured. In another aspect, the device is adapted to measure biomechanical measurements of normal and lesion-rich regions of the mouth (cheek, tongue, gingiva); rectum (assessment of fecal incontinence, rectal tumors, polyps); airway (trachea); or gastrointestinal tract (esophagus, stomach, duodenum, small intestine, large intestine); cardiovascular (heart, arteries or veins); or bladder (bladder wall compliance and degree of detrusor muscle wall aging), and is adapted for deployment via a catheter.

In another embodiment, the present invention includes a method for analyzing skin elasticity comprising: obtaining a device for analyzing a skin elasticity comprising: a wand assembly having a vacuum source, one or more holes, a probe, a proximity sensor (e.g., optical or infrared) aligned with the one or more holes, and a raised area surrounding the one or more holes; an electronic control unit configured to record the distance of the skin from the proximity sensor and calculate a deformation of the skin before, during and after a vacuum is applied in the probe; inserting the device for analyzing the skin elasticity into a body cavity; measuring a distance between the one or more proximity sensors and the skin before, during and after release of the vacuum to obtain a skin elasticity data, within and outside the probe; and analyzing the recorded skin elasticity data to determine the skin elasticity, wherein the processor calculates the skin elasticity based on the distance to the one or more proximity sensors over time throughout a measurement cycle both inside and outside the probe. In one aspect, the raised area surrounds the hole and further comprises a polished surface that provides improved contact with the skin during operation. In another aspect, the device further comprises a vacuum release line in fluid communication with the one or more holes of the probe to provide fresh air to refill the probe after a test under vacuum. In another aspect, the device further comprises an accelerometer or gyroscope that measures the relative angle of the probe between a vertical and horizontal position. In another aspect, the skin elasticity data further comprises measuring and recording a skin movement, a change in vacuum pressure, and an increment of time. In another aspect, the method further comprises analyzing the data recorded by the device is used to generate a visual representation of the skin elasticity. In another aspect, the step of measuring the skin elasticity using the wand assembly further comprises the steps of pulling and releasing a vacuum through the opening, and measuring the deformation between the skin and the proximity sensor with or without the vacuum over time to determine the skin elasticity. In another aspect, the proximity sensor comprises an infrared or optical sensor capable of detecting an extent and a shape of skin deflection over time without contacting the skin being measured. In another aspect, the probe further comprises at least one orifice that comprises a membrane to determine the rheological properties of a liquid on or about the skin. In another aspect, the skin elasticity data is further processed by at least one of: assessing a deformation of the skin under load; matching the compliance of a surgical mesh to that of the vaginal wall in order to enhance healing; or predicting the effects of remote perturbations of the pelvic organs (abdominal pressure, pelvic bending and twisting) on a vaginal configuration. In another aspect, the device is adapted to measure biomechanical measurements of normal and lesion-rich regions of the mouth (cheek, tongue, gingiva); rectum (assessment of fecal incontinence, rectal tumors, polyps); airway (trachea); or gastrointestinal tract (esophagus, stomach, duodenum, small intestine, large intestine); cardiovascular (heart, arteries or veins); or bladder (bladder wall compliance and degree of detrusor muscle wall aging).

In another embodiment, the present invention includes a device for measuring skin elasticity comprising: a probe comprising one or more holes, a vacuum source, a pressure sensor, and one or more infrared or optical proximity sensors aligned about the one or more holes, wherein the probe further comprises a raised area surrounding the one or more holes; and a processor for recording the deformation of the skin using a control unit comprising a microcontroller connected to the one or more infrared or optical proximity sensors and the one or more pressure sensors, wherein the one or more infrared or optical proximity sensors are positioned at a pre-determined distance from the skin, wherein a vacuum in the probe is capable of pulling skin into the one or more holes and the one or more infrared or optical proximity sensors are capable of measuring an amount of skin drawn into and out of the one or more holes to determine the distance between the one or more proximity sensors and the skin before, during and after release of the vacuum, and wherein the processor calculates the skin elasticity of the skin based on the distance to the one or more proximity sensors throughout a measurement cycle both inside and outside the probe.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
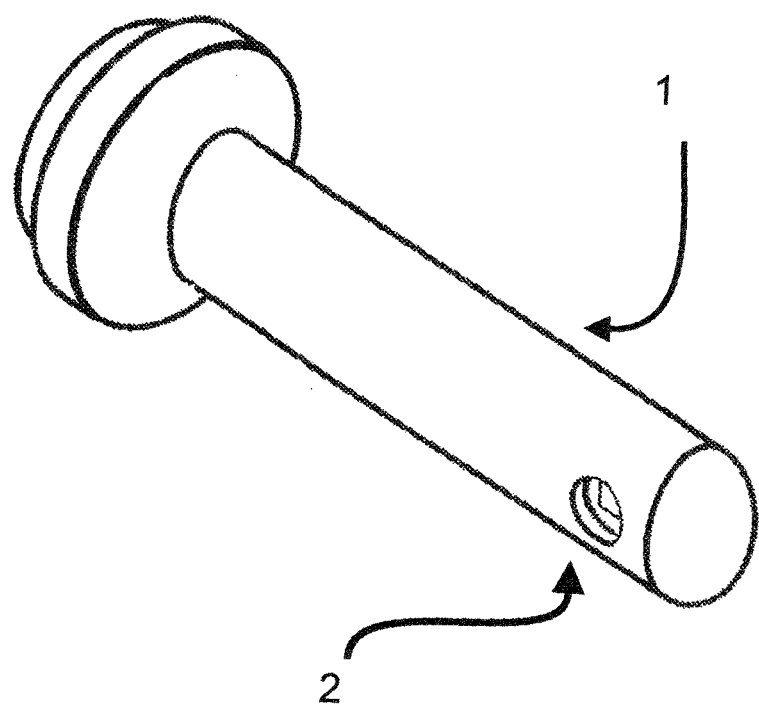
FIG. 1 shows a preferred embodiment of the probe that is inserted into the vagina.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention relates to an apparatus that measures the elasticity of skin without contacting the region to be measured, that is, the present invention is an apparatus and method for measuring skin elasticity that is contactless or touchless. Skin elasticity is measured to determine the effects of medications, skin creams, surgery procedures and the effects of aging. The present invention is designed, e.g., to measure the skin elasticity of the inner walls of the vagina to detect changes in the integrity of connective tissues in the vagina by measuring skin deflection over time without placing any materials on the surface of the inner walls of the vagina. The only portion of the apparatus and method that touches the inner walls of the vagina next to the region to be measured is the raised portion of the probe that surrounds the opening, which raised portion improves the vacuum seal between the probe and the skin. The present invention includes a small probe that allows a physician to easily perform elasticity measurements on patients during a regular office exam. Thus, the present invention provides the physician with a medical device to determine, among other conditions, if a woman is susceptible to prolapse, a condition that happens when the bladder falls down into the vagina. As shown in the figures hereinbelow, as much information is obtained from the rebound of the skin surface back into the body as from the skin leaving the opening, in particular, as regards the tissue underlying the skin. Both provide important and distinct information about skin elasticity, which cannot be obtained using presently available devices.

Skin elasticity is calculated from the data derived from the combination of vacuum pressure, time, the amount of skin pulled by the vacuum, the length of time the skin returns to the original shape, and the recoil reaction of the skin. The values are collected, calculated, and stored by the microcontroller unit or MCU and then down loaded to a computer through a data port or USB port. The data can be compiled by a computer program to display tables, plot graphs, indicate changes in the vaginal wall elasticity and assist physicians to diagnose any change of elasticity and the probability of prolapse and other conditions related to vaginal disease.

The present invention is not limited to the vagina skin elasticity measurement. The present invention can test elasticity of any skin on any area of the body of any living animal. The present invention will also test the elasticity of flexible materials such as rubber, vinyl, foams or other elastic materials.

FIG. 1 depicts a hollow tube that is oval. The wide part of the oval is 0.75 inches while the narrow part of the oval is 0.625 inches. The probe 1 is 5.5 inches in length and is the outer part of the wand assembly. A hole 2 has a 10 millimeter diameter and is on the 0.75 inch surface of the probe. Hole 2 centerline is 0.75 inches from the rounded end of the probe 1. The hole 2 allows the skin that is under test to pull down into the hole when a vacuum is applied. As the skin is pulled in the hole, the proximity sensor of FIG. 2 makes measurements as described later herein. The proximity sensor can be an infrared proximity sensor that is pulsed at a high frequency and then measures the number of reflections that return in a certain time frame. One such infrared proximity sensor is a Vishay infrared proximity sensor (e.g., part number VCNL 4000). This part can be replaced with any comparable infrared proximity sensor, e.g., the VCNL4020 model that provides added features. Further, the proximity sensor may be positioned at the end of the probe (in a handle of the probe) with measurements taken via a fiber optic cable that extends from the proximity sensor to the opening in the probe. The infrared sensor has the advantage of also providing temperature information about the skin tested. Thus, the probe portion can be completely disposable (as it contacts the patient), while the handle that contains the electronics, electrical power, vacuum source, etc., can be reused. The proximity sensor can also be an optical sensor or an ultrasound sensor. The probe 1 has a flange that allows for a vacuum seal when connected to the handle of FIG. 2. The probe 1 is removed from the handle of FIG. 2 to clean and sterilize after use.

Figure 2:
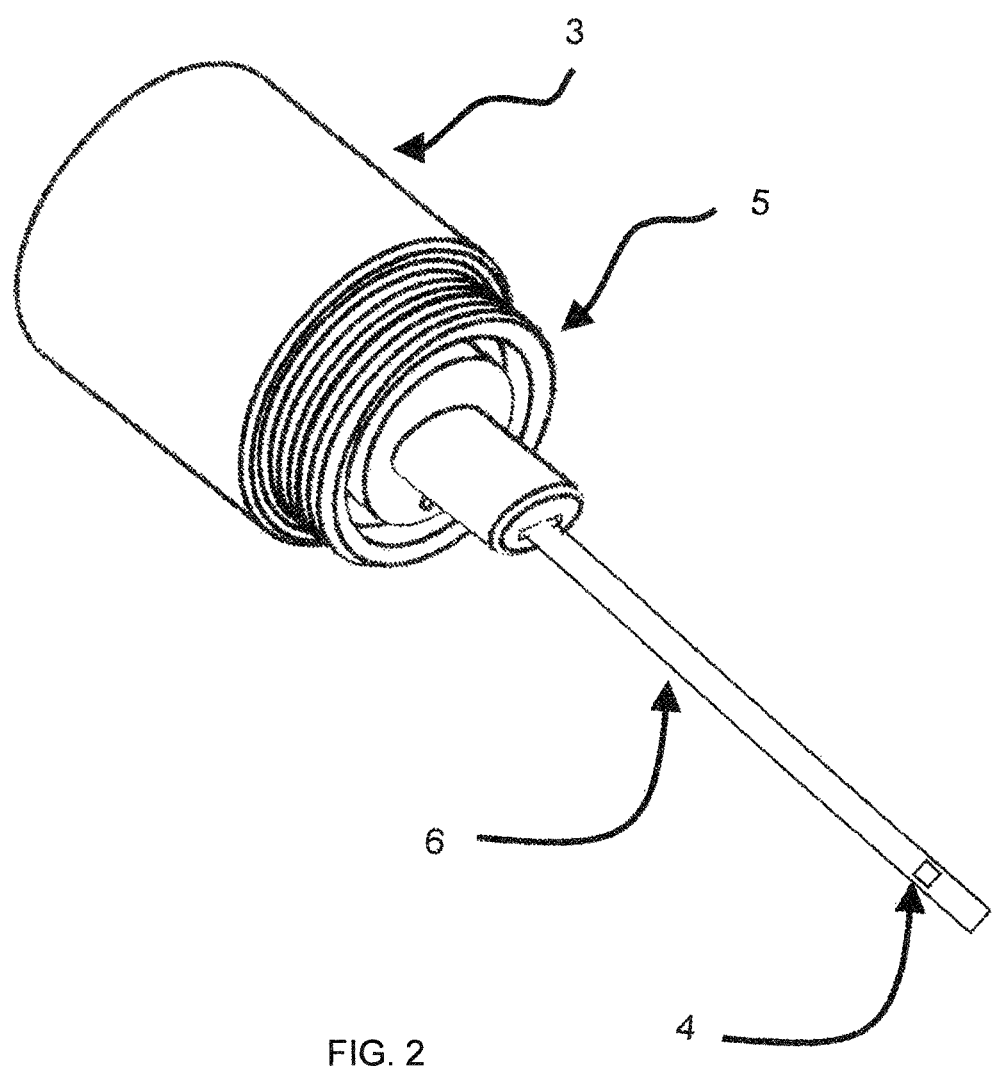
FIG. 2 shows a preferred embodiment of the handle, which attaches to the probe.

FIG. 2 shows the handle 3 with the proximity sensor 4 attached to a circuit board. The handle 3, is 2.75 inches in length and is 2.25 inches in diameter. The probe 1 of FIG. 1 attaches to the handle 3 by the threads 5 to securely hold the probe of FIG. 1 to the handle 3 and make a seal to prevent vacuum leaks. The proximity sensor 4 is precisely positioned beneath the 10 millimeter hole of FIG. 1 when the handle 3 and probe 1 are attached. The sensor circuit board 6 makes an electrical and data connection to the proximity sensor 4.

Figure 3:
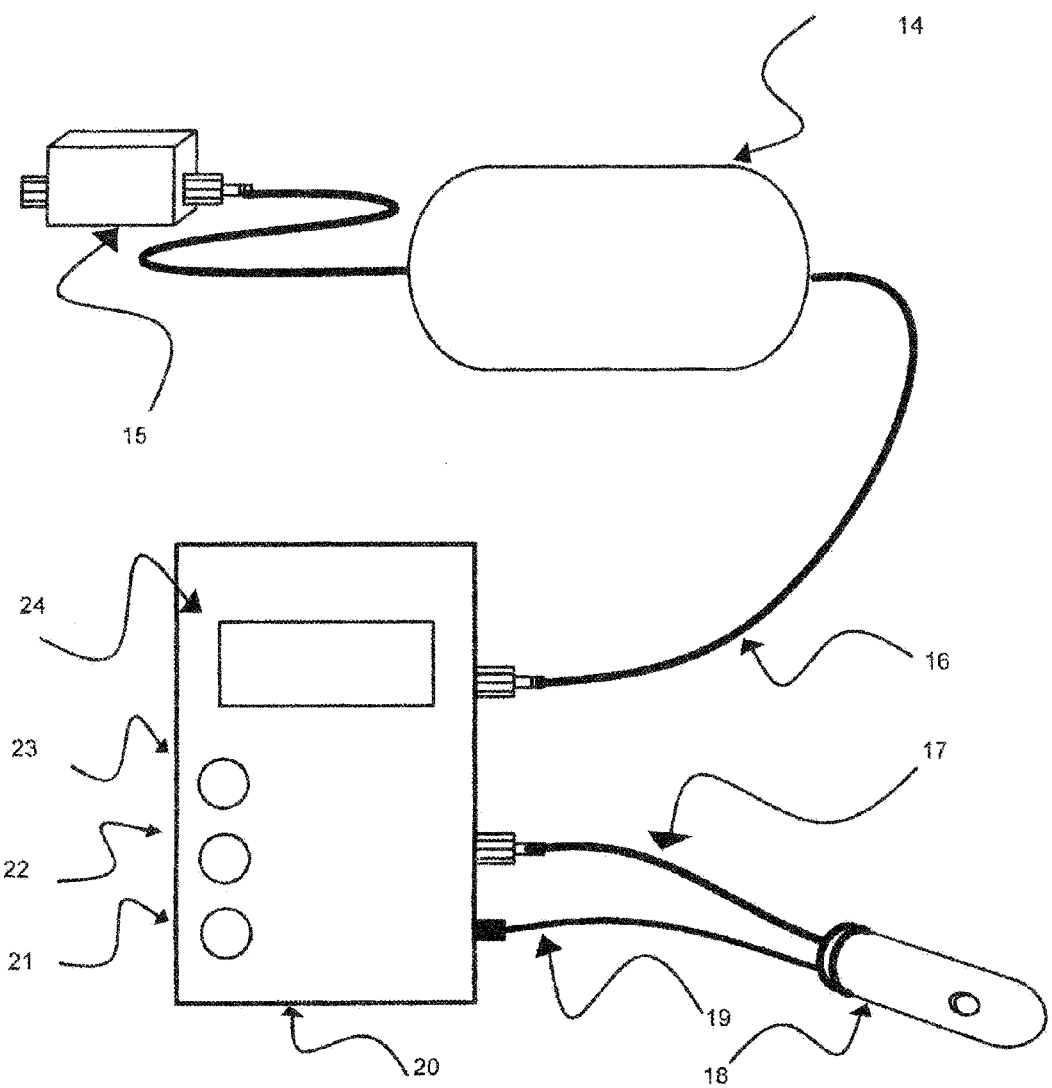
FIG. 3 is an illustration of the components of the present invention.

FIG. 3 is an illustration of the components used by the present invention to test skin elasticity. Vacuum canister 14 is evacuated to a predetermined value by an electrical vacuum pump 15. A vacuum line 16 is connected to the electronic control unit 20. Electronic control unit 20 has a liquid crystal display (LCD) 24, and switches 21, 22, and 23. The switches 21, 22, 23, and LCD 24 are used to perform menu selections displayed on the LCD screen 24 as described later in FIGS. 4A, 4B, 4C, and 4D. The data cable 19 of wand assembly 18 provides electrical and data connection between the wand assembly 18 and the electronic control unit 20. Data cable 19 is used to transmit serial data from the proximity sensor 4 of FIG. 2 to the microcontroller unit (MCU) 95 described later in FIG. 6. Vacuum line 17 is connected to the wand assembly 18 and to the electronic control unit 20. The vacuum line 17 allows a vacuum that is regulated by the control unit 20. The vacuum pump 15 and vacuum storage canister 14 are contained in the control unit 20. The electronic control valves 88, 89 and 91 of FIG. 5A are located in the control unit 20.

Figure 4A:
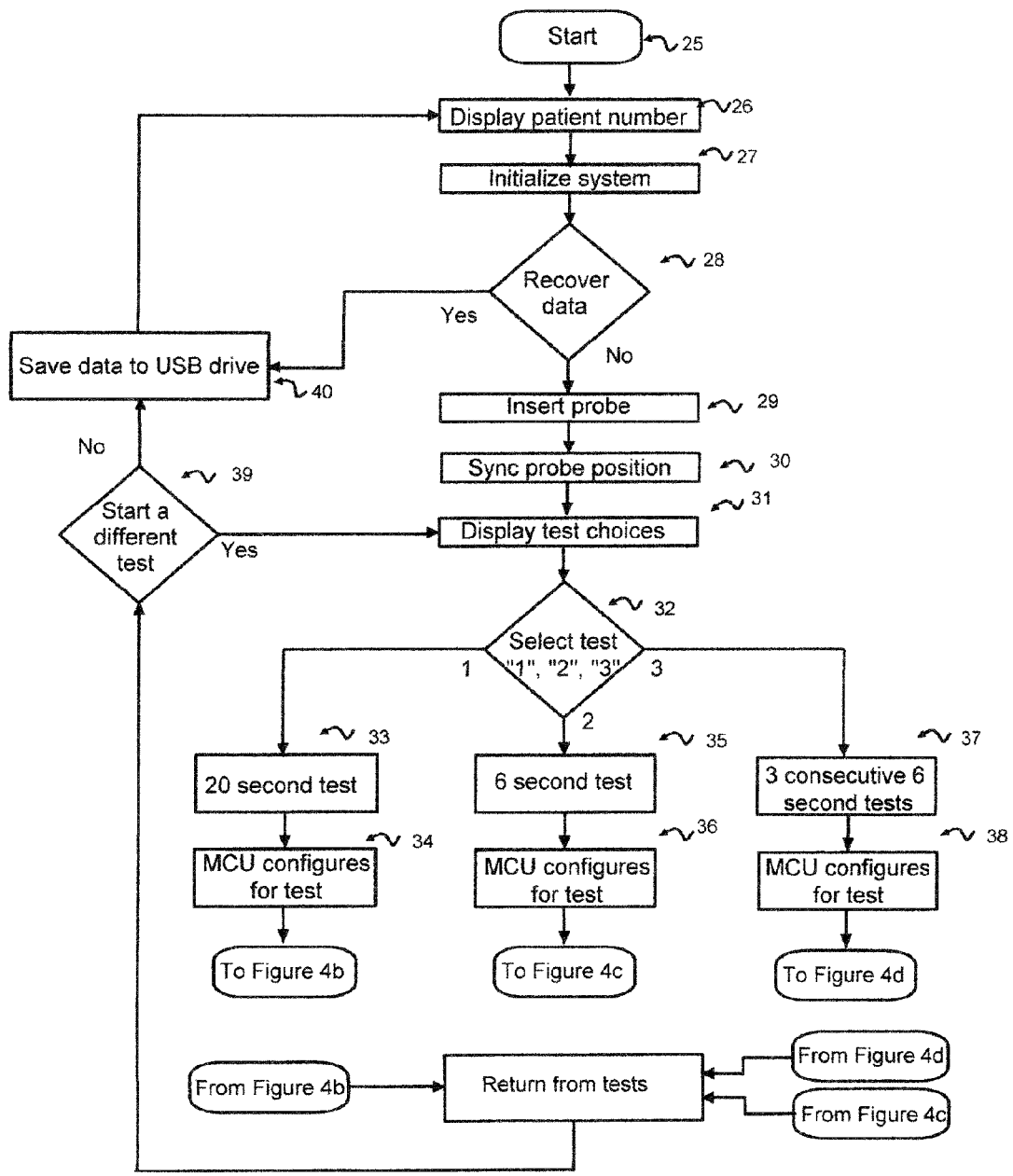
FIGS. 4A, 4B, 4C, and 4D set forth a flow chart of the control unit of the preferred embodiment.
Figure 5A:
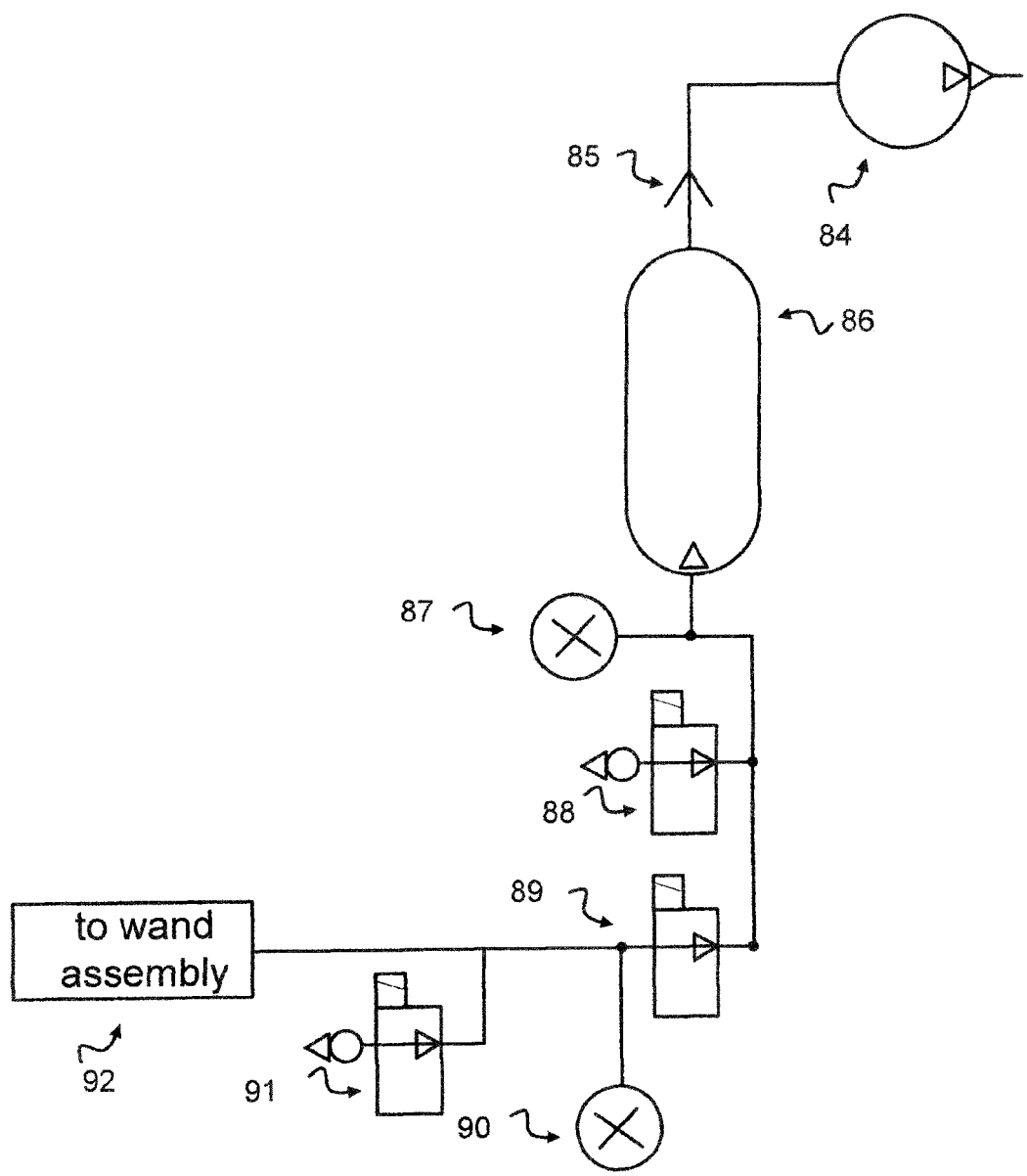
FIG. 5A is a schematic of pneumatic vacuum system of the present invention.
Figure 5B:
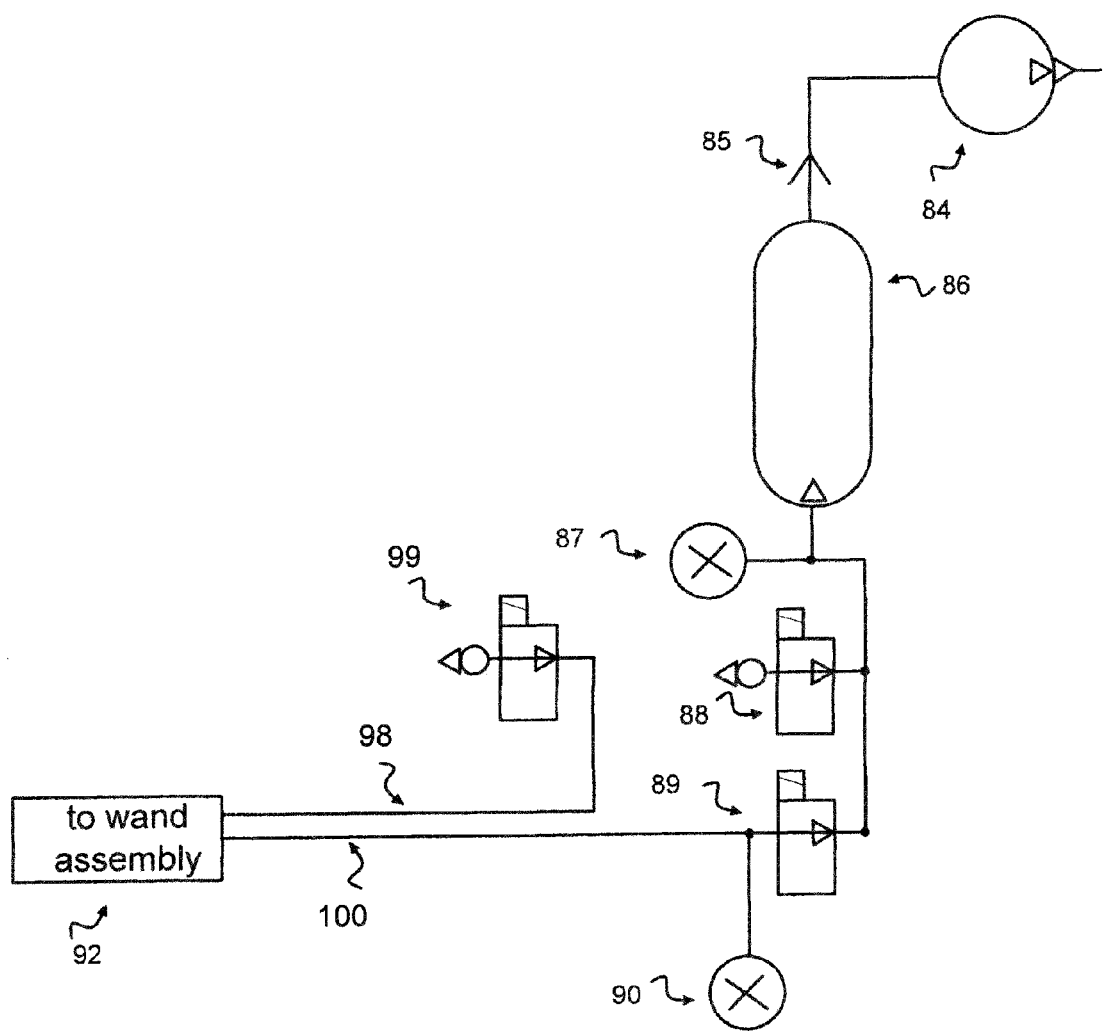
FIG. 5B shows another embodiment that shows the addition of a vacuum release valve that provides a source of clean air that refills the probe after each vacuum test.
Figure 6:
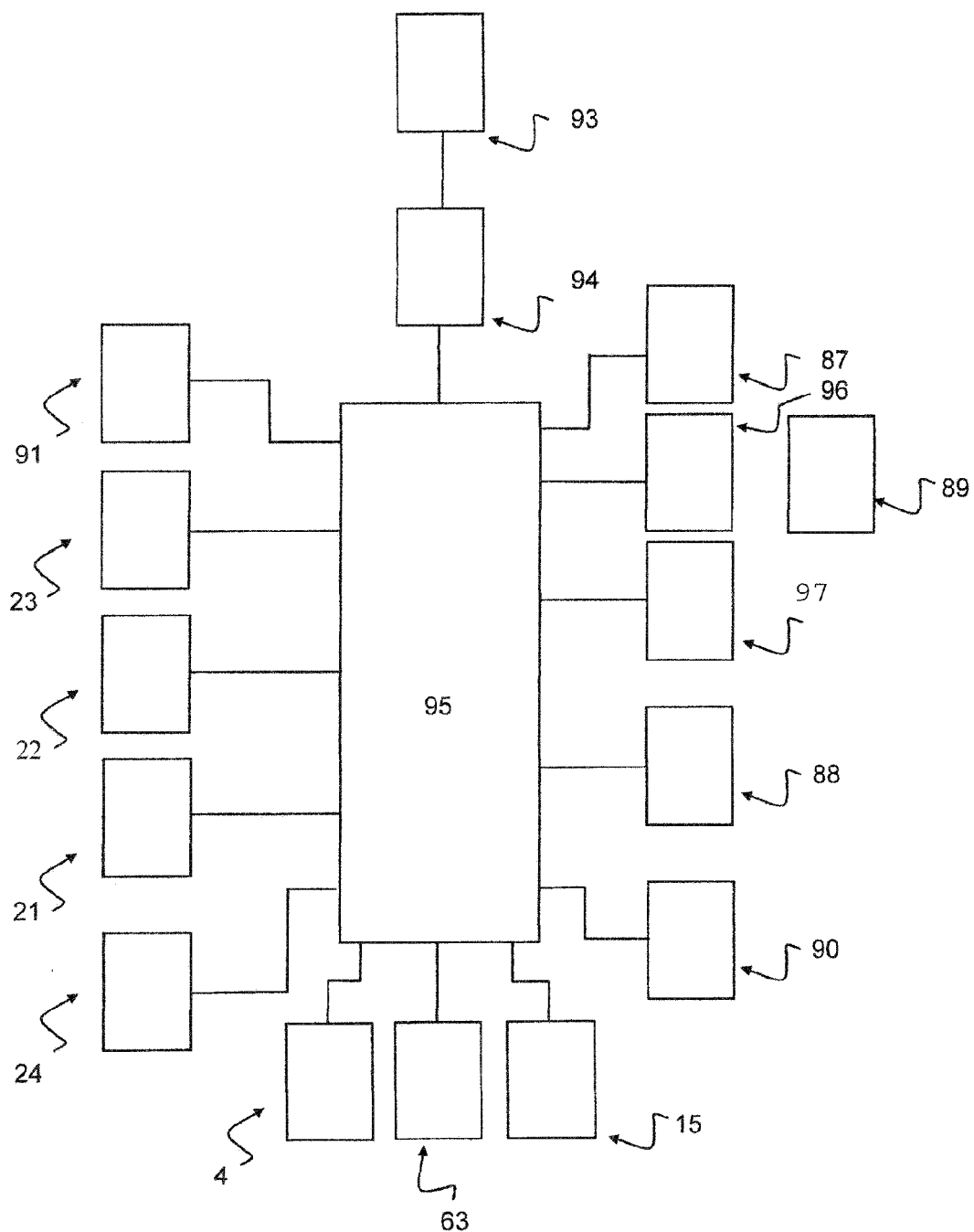
FIG. 6 is a block diagram of the microcontroller and the electrical components of the present invention.

FIGS. 4A, 4B, 4C, and 4D illustrate operational flow diagrams of the present invention. The flow diagrams describe only three of a plurality of skin elasticity tests that the present invention can perform. Referring to FIGS. 1 to 6, a microcontroller of the present invention is programmed to read and write the control values of the proximity sensor 4 of FIG. 2, the vacuum pump 15, the liquid crystal display 24 of FIG. 3, and the electronic vacuum valves 88, 89 and 91 of FIG. 5A. Referring to FIG. 4A, the power is switched on at the step 25. At step 26 the on board memory is accessed to retrieve the next patient number to be displayed on the LCD 24 of FIG. 3 screen. At step 27, the USB drive 63 of FIG. 6, is synchronized to the MCU 95 of FIG. 6, the proximity sensor 4 of FIG. 2 is initialized, the graphic display 97 of FIG. 6 is initialize, and the vacuum pump 15 of FIG. 3 energized and begins aspirating a vacuum in canister 14 of FIG. 3. At step 28, the physician is given a choice to recover data from the previous test or to continue with the current test. If the previous test was interrupted by a loss of power the all the data recorded up to the power outage will be recovered and saved to the USB drive 63 of FIG. 6 drive at step 40. The probe 1 of FIG. 1 is inserted in the body cavity at step 29. A synchronization step (Sync) begins testing the position of the probe in relation to the distance measured to the skin at step 30. When the probe is in the proper position the LCD 24 of FIG. 3 displays the test choices at step 31. The test is selected at step 32 by pressing one of the select switches 21, 22, or 23 of FIG. 3 that represents one of the test choices. Pressing one of the switches 21, 22, 23 can lead to a pre-selected program having a defined set of timed parameters, a few non-limiting examples follow. In one non-limiting example, switch 23 can select a 20 second test at step 33. At step 34, the MCU 95 of FIG. 6, configures the system for the 20 second test. In another example, switch 22 can select a single 6 second test at step 35. At step 36, the MCU 95 of FIG. 6 configures the system for the single 6 second test. In another example, switch 21 can select a 6 second test that is repeated 3 consecutive times at step 37. At step 38, the MCU 95 of FIG. 6 configures the system for the 6 second test that is repeated 3 consecutive times. The skilled artisan will recognize that these are merely illustrative examples of the length of testing, number of tests, variability on either the length or times tested, and/or the length of time between the tests. For example, the test can be 1, 2, 3, 4, 5, 6, 7, 8, 9, 10, 11, 12, 13, 14, 15, 16, 17, 18, 19, 20, 25, 30, 35, 40 or more seconds in length, which tests can have the same length, or can be random, increasing, decreasing, or intermittent. Likewise, the test can be conducted a single time, or 2, 3, 4, 5, 6, 7, 8, 9, 10, 11, 12, 13, 14, 15, 16, 17, 18, 19, or even 20 times. The length time between tests can be varied as well, 1, 2, 3, 4, 5, 6, 7, 8, 9, 10, 11, 12, 13, 14, 15, 16, 17, 18, 19, 20, 25, 30, 35, 40 or more seconds in length, which spacing between tests can have the same length, or can be random, increasing, decreasing, or intermittent.

Figure 4B:
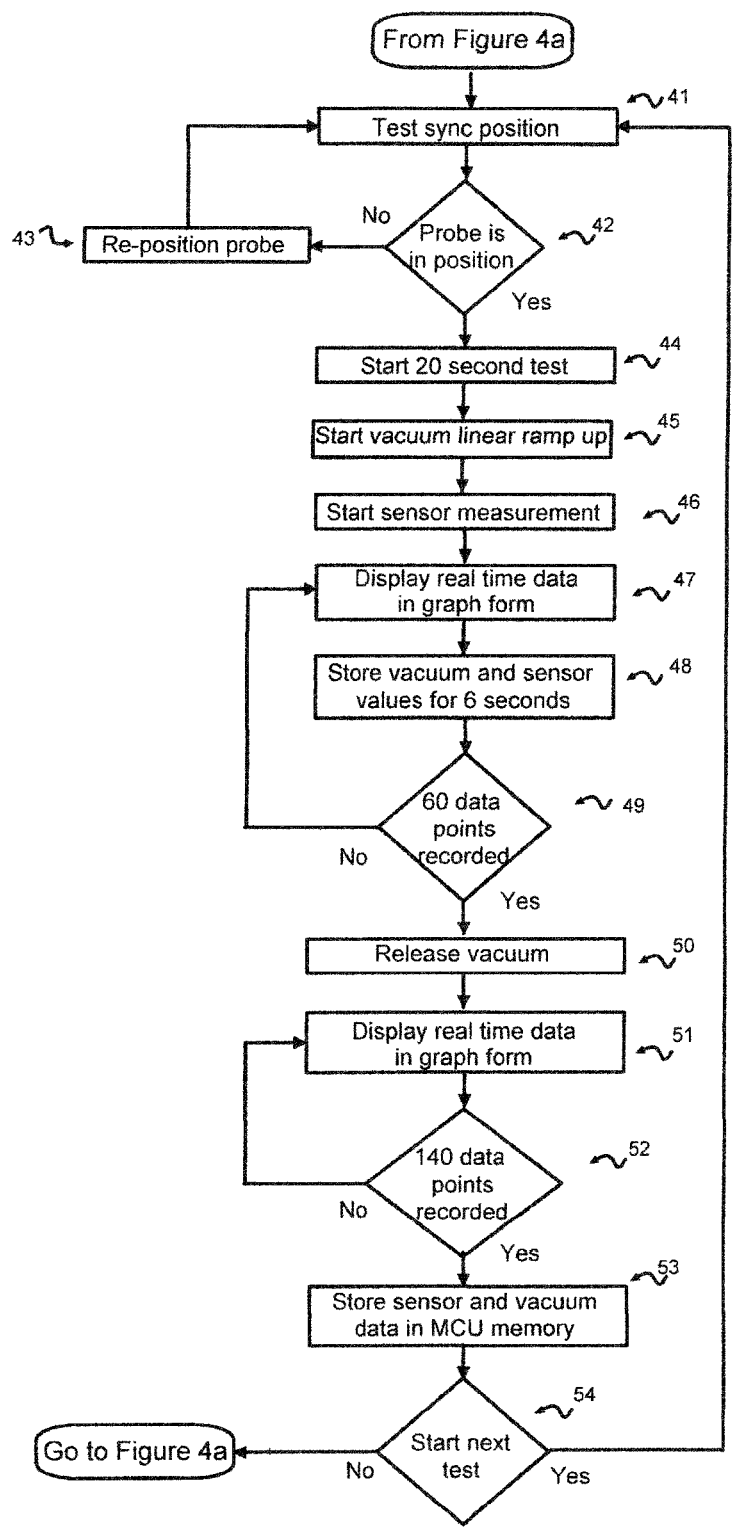
Figure 4C:
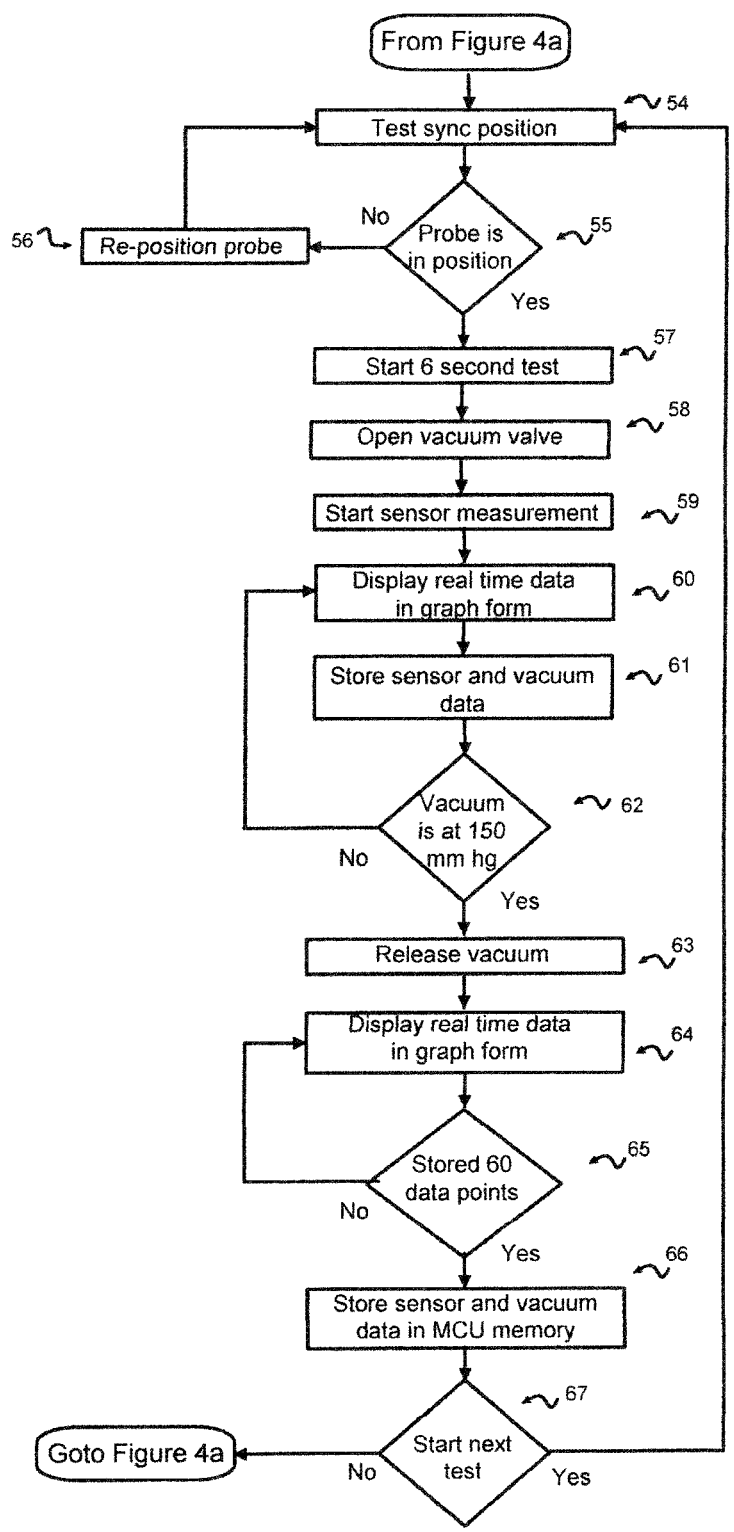
Figure 4D:
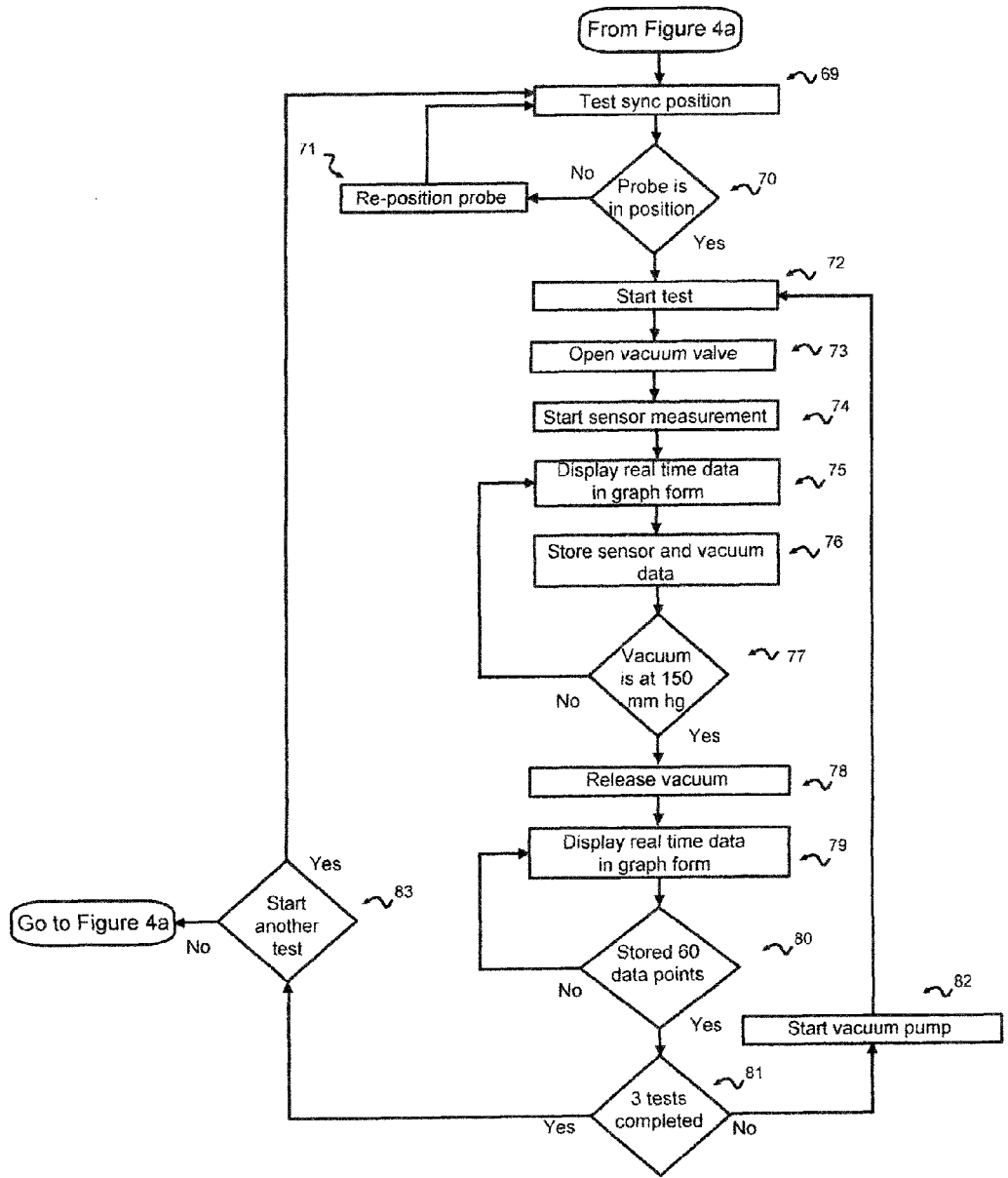

As discussed in greater detail in FIGS. 4B to 4D a series of steps are programmed for testing. The value of the vacuum pressure in storage canister 14 of FIG. 3 is checked. The digital vacuum sensor 87 of FIGS. 5A and 5B outputs an analog signal proportional to the vacuum pressure. The signal is converted to a digital value in the microcontroller. If the vacuum pressure is below a predetermined value the vacuum pump 15 of FIG. 3 is energized. When the vacuum pressure reaches the predetermined value in the storage canister, the vacuum pump 15 of FIG. 3 is switched off. The proximity sensor 4 of FIG. 2 is energized and begins outputting measurements data for sync. When the selected test has completed, the decision step 39 directs the physician to return to step 31 and select a different test or to finish the tests and save the data to the USB drive 24 of FIG. 6. After saving the test data at step 40, the patient number of step 26 is locked and saved in nonvolatile memory of the MCU 95 of FIG. 6 which prevents another test to be performed using the same patient number.

At step 41 of FIG. 4B, the sync measurements are checked. Sync assists the physician to determine an accurate probe placement before the test begins. When 10 consecutive sync values fall within a predetermined range the test automatically starts at step 42. If the sync indicates the probe is not in position, then at step 43 the probe must be repositioned to prevent distorted measurements. At step 44, the variable solenoid valve 89 of FIGS. 5A and 5B is energized and a vacuum is created in the wand assembly 92 of FIGS. 5A and 5B. A small portion the inner wall of the vagina begins to pull into the hole 2 of FIG. 1. The vacuum sensor 90 of FIGS. 5A and 5B begins sensing the change from atmospheric pressure to a vacuum. This test requires the vacuum pressure to step down from 0 to −150 mm/hg in a linear mode over 6 seconds. At step 45 the MCU 95 of FIG. 6 checks the vacuum pressure at $\frac{1}{10}$ of a second intervals and computes the correct digital vacuum value for each interval. If the vacuum value in an interval is not correct the MCU 95 of FIG. 6 compensates by changing the current imposed on the variable solenoid valve 89 of FIGS. 5A and 5B. The aperture opening in the variable solenoid valve 89 of FIGS. 5A and 5B increases as the current increases and decreases as the current decreases which causes an air flow regulation in the probe. Simultaneously, at step 46 the proximity sensor 4 of FIG. 2 sends measurement data to the MCU at $\frac{1}{10}$ of second intervals. At step 47 the graphic display 97 of FIG. 6 begins charting a real time graph displaying the relationship of skin being pulled into the hole 2 of FIG. 1 vs. time. Simultaneously, the vacuum and proximity sensor values are saved in the MCU random accessed memory (RAM) at step 48. When 60 data points are recorded by the MCU at step 49 the solenoid valve 91 of FIG. 5A is energized causing the vacuum to go to 0 at step 50. The data points continue to be charted by the graphic screen at step 51 and stored in RAM for an additional 14 seconds or 140 data points of proximity data. When 140 vacuum data points and 140 data points of proximity data are reached at step 52 the proximity and vacuum data is stored in nonvolatile memory at step 53. Additional tests are selected at step 54 or the physician can select a different tests profile at step 39 of FIG. 4A. If the tests are completed, the data can be saved to a USB drive at step 40 of FIG. 4A.

FIG. 4C describes a flow chart to perform a 6 second test. Steps 27 through 31 of FIG. 4A are repeated to initially prepare the present invention for the test. At step 32 on FIG. 4A, the 6 second test is selected at step 35 by pressing button 22 of FIG. 3. The MCU 95 of FIG. 6 configures the system for the 6 second test at step 36, by checking the value of the vacuum pressure in storage canister 14 of FIG. 3 with the digital vacuum sensor 87 of FIG. 5. The sensor outputs an analog signal proportional to the vacuum pressure. The sensor analog voltage is converted to a digital value in the MCU. If the vacuum pressure is below a predetermined value the vacuum pump 15 of FIG. 3 energized. When the vacuum pressure in the storage canister, reaches the predetermined value the vacuum pump 15 of FIG. 3 is switched off. The proximity sensor 4 of FIG. 2 is energized and begins outputting measurement data for sync. At step 55, the sync measurements are checked. When 10 consecutive values at step 56 fall within a predetermined range the test automatically starts at step 57. If the sync indicates the probe is not in position, then at step 56 the probe must be repositioned to prevent distorted measurements. At step 58 variable solenoid vacuum valve 89 of FIGS. 5A and 5B is fully opened and a vacuum is created in the wand assembly. A small portion the inner wall of the vagina begins to pull into the hole 2 of FIG. 1. In step 59, the vacuum sensor 90 of FIGS.

5A and 5B begins sensing the change from atmospheric pressure to a vacuum. At step 60 the proximity sensor 4 of FIG. 2 begins sending data to the MCU at $\frac{1}{10}^{th}$ of a second intervals. At step 60 the graphic display 97 of FIG. 6 starts charting a real time graph displaying the relationship of skin being pulled into the hole 2 of FIG. 1 vs. time. The data from the vacuum sensor 90 of FIGS. 5A and 5B and the proximity sensor 4 of FIG. 2 are stored in the RAM of the MCU at step 61. In step 62, a decision point is reached that determines if a pre-determined vacuum value has been reached (e.g., 150 mm Hg). For example, in less than 1 second the predetermined vacuum value can be reached at step 63 and the MCU switches off the variable solenoid valve 89 of FIGS. 5A and 5B and energizes solenoid valve 91 of FIG. 5A at step 63 to release the vacuum. The graphic display continues charting the data at step 64 until 60 proximity sensor data values and 60 vacuum values (step 65) have been recorded to RAM of the MCU. The data are stored in nonvolatile memory in the MCU at step 66. Additional tests are selected at step 67 or the physician can select a different test profile at step 39 of FIG. 4A. If the tests are completed, the data can be saved to a USB drive at step 40 of FIG. 4A.

FIG. 4D flow chart describes the steps of the present invention to perform three consecutive 6 second tests. Each test consists of 180 data points of proximity sensor 4 of FIGS. 2 and 180 data points of vacuum sensor 90 of FIGS. 5A and 5B. Steps 27 through 31 of FIG. 4A are repeated to initially prepare the present invention for the test. At step 32 on FIG. 4A the 3 consecutive 6 second test is selected at step 37 by pressing button 21 of FIG. 3. The MCU 95 of FIG. 6 configures the system for the three consecutive 6 second test at step 38 on FIG. 4A, by checking the value of the vacuum pressure in storage canister 14 of FIG. 3 with the digital vacuum sensor 87 of FIGS. 5A and 5B. The sensor outputs an analog signal proportional to the vacuum pressure. The sensor analog voltage is converted to a digital value in the MCU. If the vacuum pressure is below a predetermined value the vacuum pump 15 of FIG. 3 energized. When the vacuum pressure reaches the predetermined value in the storage canister, the vacuum pump 15 of FIG. 3 is switched off. The proximity sensor 4 of FIG. 2 is energized and begins outputting measurement data for sync. At FIG. 4D step 69 the sync measurements are checked. When 10 consecutive values at step 70 fall within a predetermined range the test automatically starts at step 72. If the sync indicates the probe is not in the correct position, then at step 71 the probe must be repositioned to prevent distorted measurements. At step 73 variable solenoid vacuum valve 89 of FIGS. 5A and 5B is fully opened and a vacuum is created in the wand assembly. A small portion the inner wall of the vagina begins to pull into the hole 2 of FIG. 1. The vacuum sensor 90 of FIGS. 5A and 5B begins sensing the change from atmospheric pressure to a vacuum. At step 74 the proximity sensor 4 of FIG. 2 begins sending data to the MCU at $\frac{1}{10}^{th}$ of a second intervals. At step 75 the graphic display 97 of FIG. 6 starts charting a real time graph displaying the relationship of skin being pulled into the hole 2 of FIG. 1 vs. time. The data from the vacuum sensor 90 of FIGS. 5A and 5B and the proximity sensor 4 of FIG. 2 are stored in the RAM of the MCU at step 76. In less than 1 second the predetermined vacuum value is reached at step 77 and the MCU switches off the variable solenoid valve 89 of FIGS. 5A and 5B and energizes solenoid valve 91 of FIG. 5A at step 78 to release the vacuum. At step 79 the proximity sensor 4 of FIG. 2 and the vacuum sensor 90 of FIGS. 5A and 5B data continue to be stored in the RAM of the MUC and charted by the graphic display. When 60 proximity sensor data values and 60 vacuum sensor data values have been recorded by the RAM of the MCU at step 80 the test ends. The decision step 81 determines if there have been 3 consecutive tests performed. If not, then another 6 second test begins by first starting the vacuum pump 15 of FIG. 3 and switching it off when the storage canister 14 of FIG. 3 reaches a predetermined vacuum at step 82 and then restart the test at step 72. If 3 tests have been performed, the physician has a choice at step 83 to restart another three consecutive 6 second test at step 69, select a different test profile at step 39 of FIG. 4A or go to step 40 of FIG. 4A and save the data to a USB drive. The present invention is not limited to the described three tests, as outlined hereinabove. A plurality of preprogrammed tests are possible to determine skin elasticity, including but not-limited to: variable time per test, variable vacuum, variable measurements, variable times between tests, and/or variable proximity.

FIG. 5A is a schematic of the pneumatic vacuum system of the present invention. The vacuum pump 84 is connected by vacuum tubing to a check valve 85 to prevent air from flowing back into the vacuum canister 86 after the vacuum pump is switched off. The vacuum canister 86 is used as a vacuum reservoir for fast evacuation of air through the vacuum system. An electronic vacuum sensor 87 is connected by tubing the vacuum canister 86 and senses the vacuum. The vacuum sensor outputs an analog voltage proportional to the vacuum pressure in the canister. The analog voltage is used by the MCU 95 of FIG. 6 to determine the vacuum pressure and keep a constant vacuum pressure in the vacuum canister 86. The MCU switches the pump on if the vacuum is lower than a predetermined vacuum value and off at a preset higher vacuum value. Solenoid valve 88 is connected by tubing to electronic vacuum sensor 87 and will release the vacuum in the vacuum canister 86. If the MCU detects a predetermined vacuum value from vacuum sensor 90, solenoid valve 88 is energized and opened to bring the vacuum system to atmospheric pressure. The outlet port on the electronic variable solenoid valve 89 is connected inline by tubing to the solenoid valve 88, and vacuum canister 86. The inlet port on the electronic variable solenoid valve 89 is connected inline by tubing to the vacuum sensor 90 and the wand assembly 92. The electronic variable solenoid valve 89 controls the vacuum pressure level that is proportional to the current applied to the solenoid valve 88 by the MCU 95 of FIG. 6. Flow restriction is one of the parameters used in an elasticity test. Solenoid valve 91 is connected by tubing to the inlet side of electronic variable valve 89 and when opened releases the vacuum pressure in the wand assembly 92. Vacuum sensor 90 is connected by tubing to the inlet side of electronic variable solenoid valve 89 and sends an analog voltage proportional to the vacuum pressure of the wand assembly 92 to MCU 95 of FIG. 6. The data values from the vacuum sensor are stored in the RAM of the MCU during tests and are used in calculating current levels to regulate the vacuum levels.

FIG. 5B shows another embodiment of the pneumatic vacuum system of the present invention. The vacuum pump 84 is connected by vacuum tubing to a check valve 85 to prevent air from flowing back into the vacuum canister 86 after the vacuum pump is switched off. The vacuum canister 86 is used as a vacuum reservoir for fast evacuation of air through the vacuum system. An electronic vacuum sensor 87 is connected by tubing the vacuum canister 86 and senses the vacuum. The vacuum sensor outputs an analog voltage proportional to the vacuum pressure in the canister. The analog voltage is used by the MCU 95 of FIG. 6 to determine the vacuum pressure and keep a constant vacuum pressure in the vacuum canister 86. The MCU switches the pump on if the vacuum is lower than a predetermined vacuum value and off at a preset higher vacuum value. Solenoid valve 88 is connected by tubing to electronic vacuum sensor 87 and will release the vacuum in the vacuum canister 86. If the MCU detects a predetermined vacuum value from vacuum sensor 90, solenoid valve 88 is energized and opened to bring the vacuum system to atmospheric pressure. The outlet port on the electronic variable solenoid valve 89 is connected inline by tubing to the solenoid valve 88, and vacuum canister 86. The inlet port on the electronic variable solenoid valve 89 is connected inline by tubing or vacuum line 100 to the vacuum sensor 90 and to the wand assembly 92. In this embodiment, the wand assembly 92 is further connected to a vacuum release line 98 that is connected to an electronic variable solenoid valve 99 that serves as a vacuum release valve that provides clean air to the wand assembly 92 that refills the probe after each vacuum test. The fresh air return or vacuum release line 98 and electronic variable solenoid valve 99 are added to allow for a clean source of air to refill the probe after each vacuum test. The fresh air return reduces the possibility of contaminates from previous tests subjects to enter the probe as the air refilled the probe after a vacuum test. Without the fresh air return line, after each test all the internal lines, valves, and connectors would need cleaning. By providing the fresh air return or vacuum release line 98, a negative air pressure pulls air from the vacuum release valve through the vacuum release line, in the probe, the vacuum line and the internal connectors and valves. Then, when the vacuum needs to be released, the variable solenoid valve 89 closes and the fresh air valve 99 opens. This brings the negative pressure back to atmosphere in the probe and through the lines up to the variable solenoid valve 89. The electronic variable solenoid valve 89 controls the vacuum pressure level that is proportional to the current applied to the solenoid valve 89 by the MCU 95 of FIG. 6. Flow restriction is one of the parameters used in an elasticity test. Vacuum sensor 90 is connected by tubing to the inlet side of electronic variable solenoid valve 89 and sends an analog voltage proportional to the vacuum pressure of the wand assembly 92 to MCU 95 of FIG. 6. The data values from the vacuum sensor are stored in the RAM of the MCU during tests and are used in calculating current levels to regulate the vacuum levels.

FIG. 6 is a block diagram that illustrates the electronic components of the present invention. MCU 95 is programmed to perform the tasks required to control all the required functions of the flow charts, FIGS. 4A, 4B, 4C, and 4D. The power is preferably a 12 volt direct current power supply 93. The power switch 94 switches on the power to the MCU 95. Vacuum solenoid valve 88 is electrically connected to an I/O port that provides power to open the valve to release the vacuum in vacuum canister 14 of FIG. 3. Vacuum sensor 87 is electrically connected to an A/D port on MCU 95 that reads the analog voltage output from the sensor and converts it to a digital signal used by the MCU 95 to switch on and off the vacuum pump 15. Digital analog converter 96 is electrically connected to the MCU 95 and converts the digital signal from the MCU to an analog value for regulating the solenoid variable valve 89. The solenoid variable valve 89 is electrically connected to the digital to analog converter 96 that varies the amount of current through the solenoid. As the current increases through the valve's solenoid, valve 89 opens wider, allowing more airflow. Solenoid valve 91 is electrically connected to an I/O port on MCU 95 and energizes the valve's solenoid at a programmed point to release the vacuum pressure on the wand assembly. In the vacuum configuration of FIG. 5B, the valve 99 opens to release the vacuum pressure on the wand assembly. Vacuum sensor 90 monitors the vacuum pressure on the vacuum line connected to the wand assembly by outputting an analog voltage to a second A/D input of MCU 95. The A/D input converts the analog signal to a digital value proportional to the analog voltage. Proximity sensor 4 is electrically connected to an I2C serial data ports on MCU 95. Data from proximity sensor 4 is used in the MCU 95 to measure the distance from the sensor 4 to the surface of the skin pulled through the hole 2 in FIG. 1 by the applied vacuum. Liquid crystal display 24 is connected to I/O ports of the MCU 95 to display the various menu options and test results that are computed by the MCU 95. Graphic display 97 is connected to a serial port on the MCU 95 to chart in real time the proximity sensor 4 data received by the MCU. Push buttons 21, 22, and 23 are electrically connected to the MCU 95 and when pressed causes various menus and operator choices to be displayed on the liquid crystal display 24 for performing the various tests. USB drive port 63 is electrically connected to MCU 95 to allow converted test data from the MCU 95 to be transferred to a USB drive. The data stored on the USB drive is down loaded to a computer that is programmed to compute, graph, and store the skin elasticity data for analysis.

Figure 7:
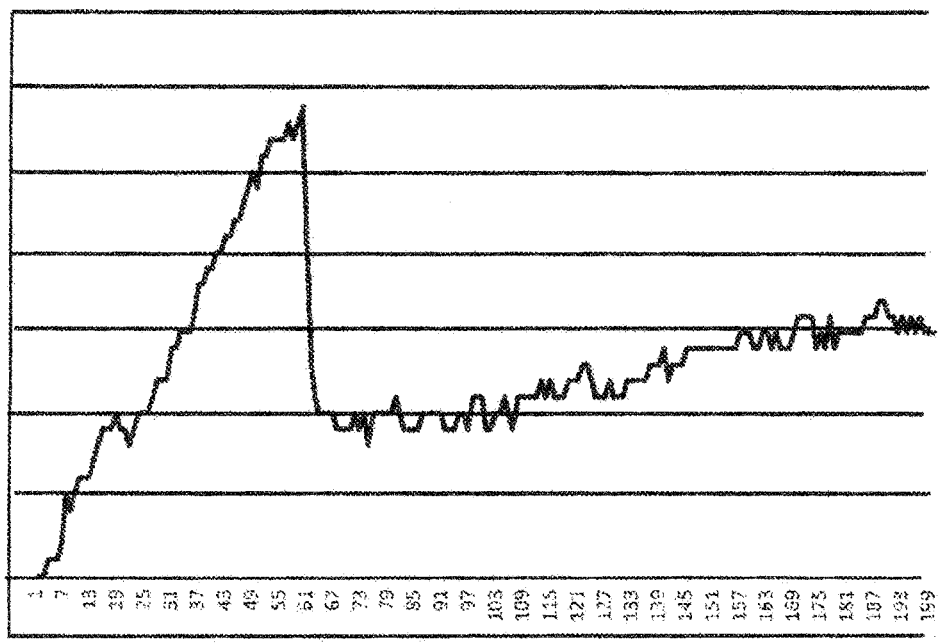
FIG. 7 is a graph representing the data of a patient with prolapse.

FIG. 7 is a graph of the deformation of the skin in the anterior wall of the vagina of a patient with prolapse. The probe was inserted 5 centimeters with the hole 2 of FIG. 1 pointing up. The test parameters were selected by choosing a menu displayed on the LCD screen 24 of FIG. 3. The test was set to a 20 second time period. The test parameters consisted of a vacuum linearly increased from 0 to 150 millimeters of mercury over a 6 second period while data measurements were recorded in $\frac{1}{10}^{th}$ of a second intervals. At the end of 6 seconds the vacuum was released. The data was continuously collected for 14 more seconds. 200 data points from the proximity sensor and 200 data points from the vacuum sensor were transferred to a USB drive through the USB drive port 63 of FIG. 6. The data stored on the USB drive is down loaded to a computer for analysis. The skin deformed to 2.9 millimeters and dropped to 0.9 millimeters in 2/10th of a second. Over the last 14 seconds the skin gradually rose to 1.5 millimeters. The chart indicates that the anterior vaginal wall of the patient did not continue relaxation to completion, a sign of altered viscoelastic properties. This can be clearly seen in comparison with the continuing vaginal wall relaxation of a patient without prolapse (FIG. 8).

Figure 8:
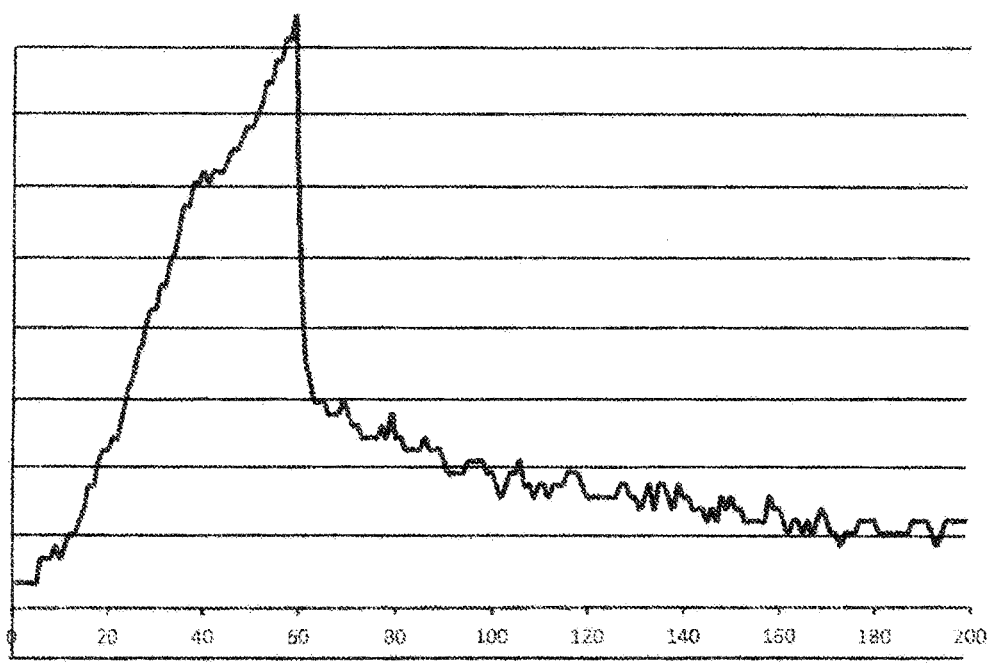
FIG. 8 is a graph representing the data of a patient without prolapse.

FIG. 8 is a graph of the deformation of the skin in the anterior wall of the vagina of a patient without prolapse. The test parameters were the same as in FIG. 7. The vacuum was increased from 0 to 150 millimeters of mercury over 6 seconds while data measurements of the proximity sensor 4 of FIG. 2 and the vacuum measurements from the sensor 90 of FIGS. 5A and 5B were recorded every $\frac{1}{10}^{th}$ of a second. The test continued for 14 seconds longer still collecting data each $\frac{1}{10}^{th}$ of a second. The plotted data show the elasticity of a patient's vagina without prolapse. The peak deformation at 150 millimeters of mercury was 2.1 millimeters with a relaxation from 0.75 millimeters that continued down to 0.25 millimeters at the end of 20 seconds. The chart indicates the skin deformation and recovery are significantly different than in the case of the patient with a prolapsed vagina.

Figure 9:
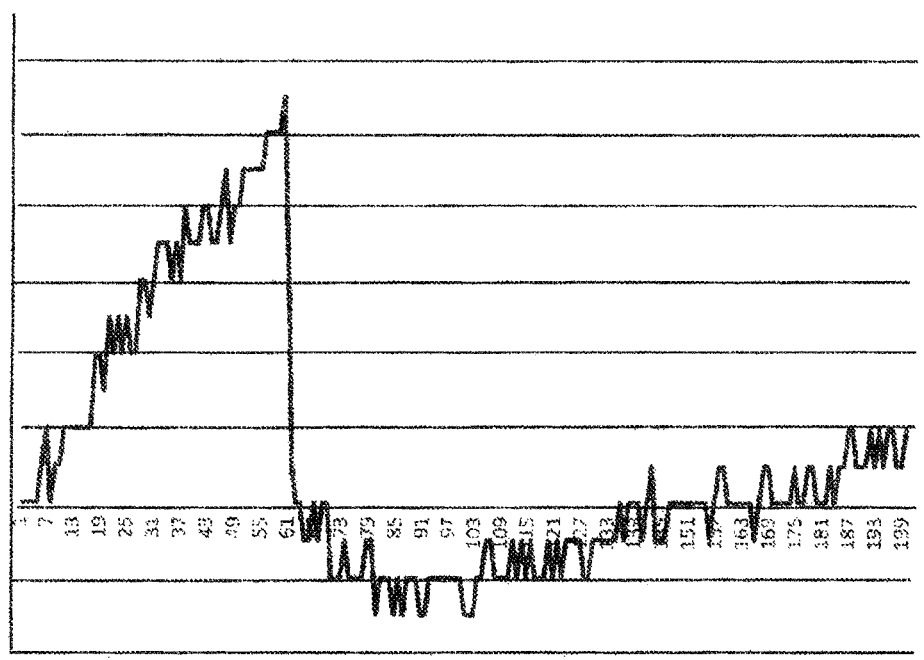
FIG. 9 is a graph representing the data of the cheek of a patient's face.

FIG. 9 is a chart of the skin deformation of the cheek on a patient's face. The same parameters and procedures were followed as in FIGS. 7 and 8. The data produced a very different graph that represents the versatility of the present invention. At the peak when the vacuum reached 150 millimeters of mercury the skin deformed to 0.55 millimeters. The vacuum was released and the skin pulled back past zero to −0.15 millimeters. At 14 seconds into the test the skin moved from −0.15 millimeters to 0. Then the skin began moving up until the test was completed at 20 seconds where the skin reached a 0.1 millimeter deflection. The patient under the test was a male approximately 60 years old. The graph indicates the skin bouncing back and passing through zero creating a concave effect on the skin surface. Tests performed on tighter skin surfaces showed a smaller skin deformation but not passing through zero. Another feature the graph depicts is the representation of the patient's heartbeat. The groupings of the spikes in the graph at 6 seconds equals to 7 indicating a slightly faster rate of 1 per second. At 20 seconds the groupings of spikes 22 beats or a slightly faster rate than 1 beat per second.

Additional modifications of the present invention included: a 4.3" diagonal graphic screen that displays the graph of the skin deformation in real time. The display is programmed to show three consecutive graphs for comparing the results. Optionally, another feature assists the clinician before each test to accurately synch the initiation of a measurement when the proximity sensor indicates the minimal amount of force applied to the probe against the skin to create a vacuum seal without deforming the skin. When the force is in range the test automatically begins. The force or proximity sensor feature improved test results and reduced the overall time for testing. Finally, a new probe was design that changed the shape and reduced the size of the probe shaft. The latest version of the probe was reduced to an approximate diameter of 0.65", which is approximately the size of a finger. The exterior of the probe can also be covered with a soft or viscoelastic material, and/or provided with one or more joints such that the probe can be flexed to provide a better fit for insertion into a body orifice or to reach a specific location with minimal discomfort or damage to underlying or adjacent tissues.

Figure 10A:
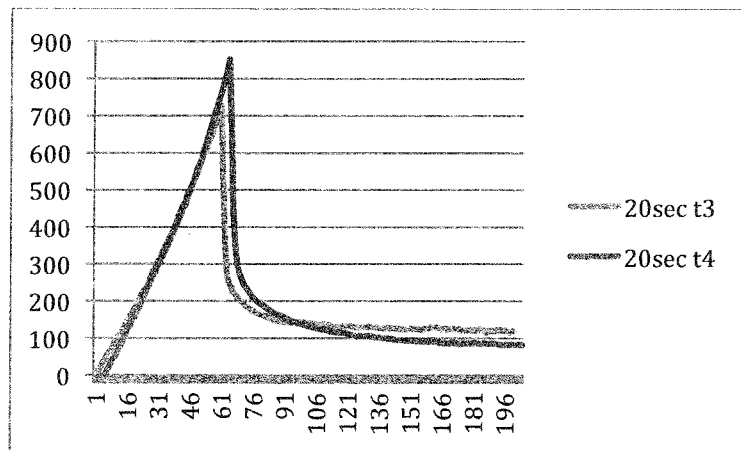
FIGS. 10A and 10B are graphs that show the results from a normal subject (FIG. 10A) and patient with vaginal prolapse (FIG. 10B).
Figure 10B:
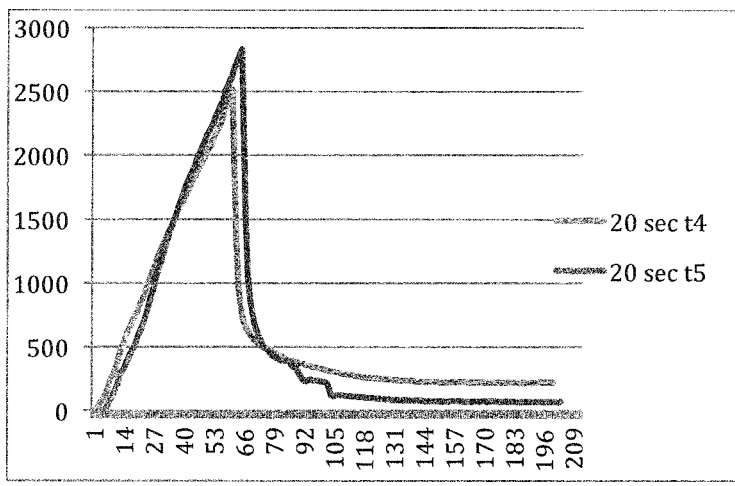

FIG. 10A is a graph that shows the data obtained from the vagina of 66-year old control patient, and FIG. 10B the data obtained from a patient with vaginal prolapse. Each test was performed at a 3 cm depth in the vagina. The tests start at 0 vacuum and ramps up to 150 mm/hg linearly over a 6 second time period. At the end of 6 seconds the vacuum is released but data continues to be recorded for an additional 14 seconds.

Figure 11A:
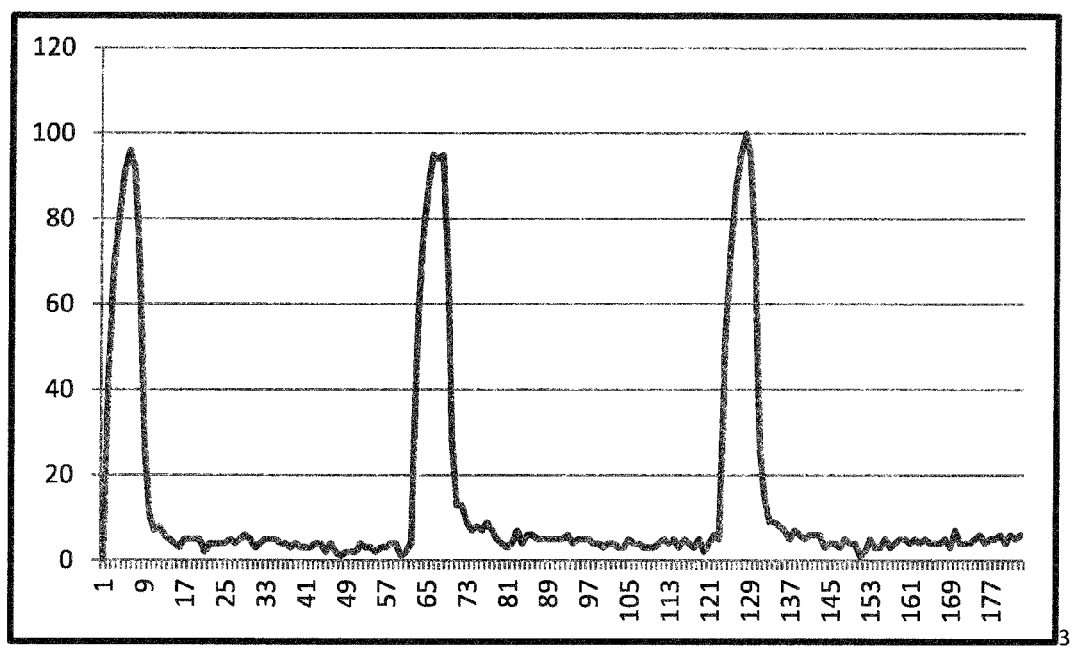
FIGS. 11A to 11C shows three different graphs showing 3 consecutive 6 second acquisitions (FIG. 11A), a 20 second acquisition (FIG. 11B), and the result of 3 consecutive 6 second overlaid acquisitions (FIG. 11C).
Figure 11B:
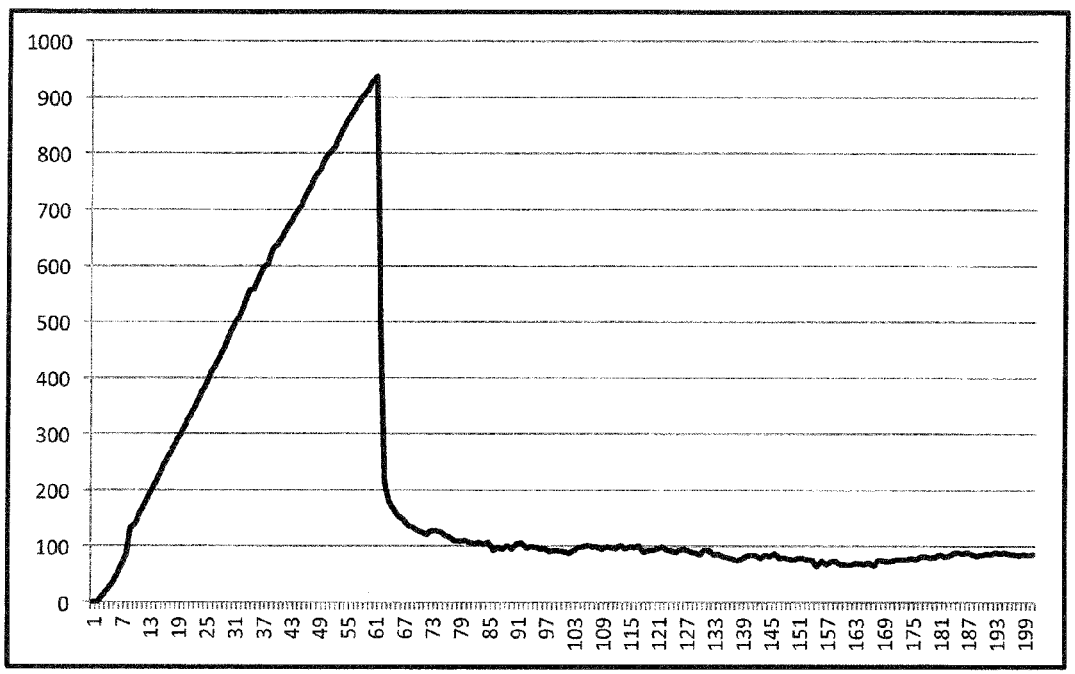
Figure 11C:
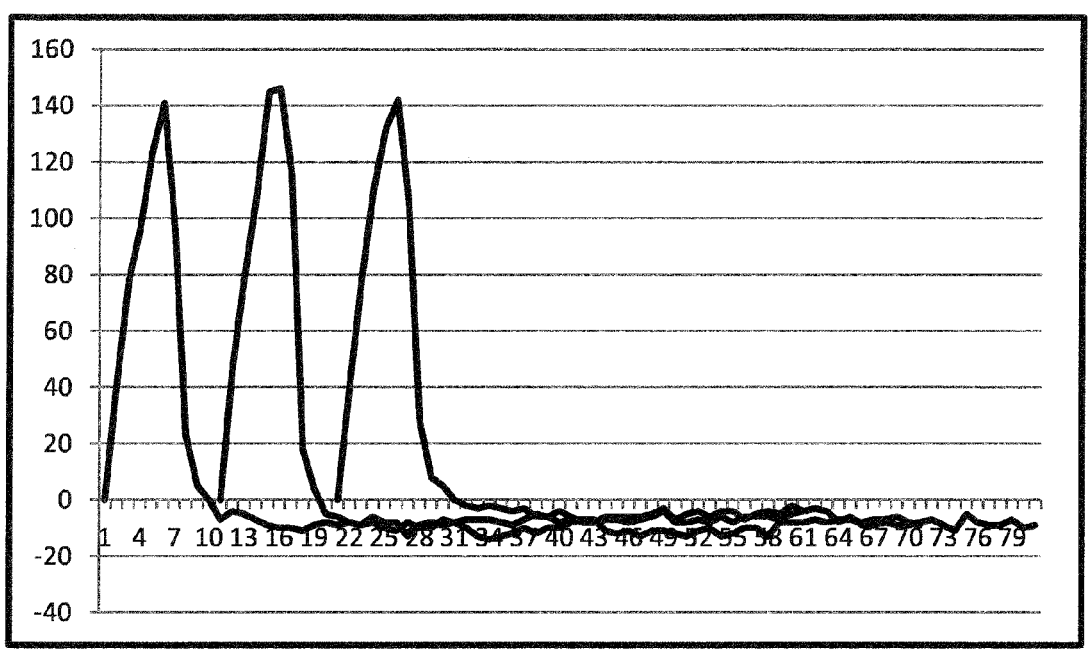

FIGS. 11A to 11C shows three different graphs showing 3 consecutive 6 second acquisitions (FIG. 11A), a 20 second acquisition (FIG. 11B), and the result of 3 consecutive 6 second overlaid acquisitions (FIG. 11C).

Figure 12A:
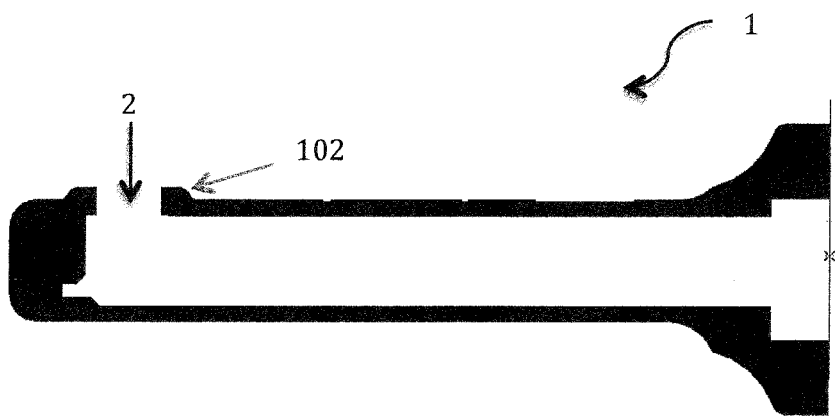
FIG. 12A is a cross-sectional side view.
Figure 12B:
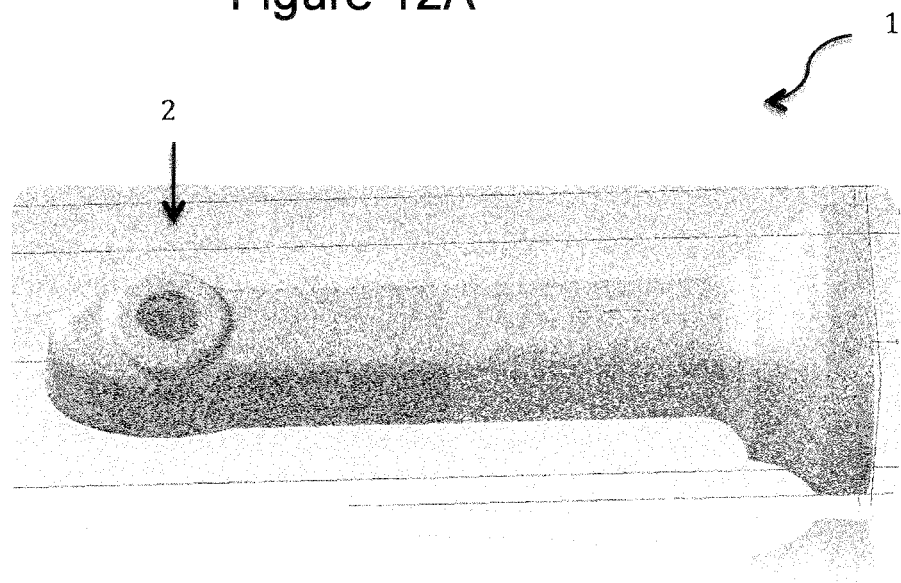
FIG. 12B is an isometric view of the probe of the present that shows a raised area surrounding the opening in the probe.

FIG. 12A is a cross-sectional side view of the probe 1 depicted with hole 2 and further including a raised area or lip 102 that generally surrounds the opening 2. FIG. 12B is an isometric view of the probe 1 of the present that shows a raised area surrounding the opening in the probe and forming a raised lip around the opening 2. In one embodiment, the hole 2 can be approximately a 10 mm hole, which can be surrounded by a raised area or lip 102 that can be raised about 0.074 inches (or 1.88 mm) above the top surface of the probe. This provides a flat surface around the hole to polish and create a better vacuum seal. In one specific embodiment, the surface of the raised area or lip 102 is polished to maximize the contact between the raised area or lip 102 and the skin during operation of the probe. Polishing the surface of the raised area or lip 102 provides an improved vacuum seal between the skin and the probe and can also reduce the possibility of damaging the skin by reducing the possibility of friction with between the surface of the raised area or lip 102 and the skin.

The probe 1 can further comprise an accelerometer or gyroscope at, e.g., the sensor board, that can be connected to the logic or processor to provide data about the overall position of the probe and that can further indicate on a screen, when the probe is level and at 0, 90, 180, and 270 degrees to assist with accurately positioning the probe. Further, the present invention does not use a Hall Effect proximity detector because the Hall Effect requires contacting the skin with a conductor, which can affect the response of the skin to the pull of the vacuum, because it obstructs the view of the skin, and because the conductive nature of skin would also provide varying results using the Hall Effect would cause too much variation in the results.

The probe of the present invention allows for in vivo, reliable and reproducible, hand-free, quantitative measurements of the biomechanical properties of the human anterior vaginal wall. These properties include elastic deformation during suction, followed by viscoelastic changes during the return to baseline.

Another optional feature of the present invention is that if the system for some reason loses power or the connection is lost during recording, the data is saved on a memory connected to the processor and the data can be retrieved at a later time. In addition, more memory can be added to the circuit board so that all the information collected in a day can be transferred immediately, or stored and processes all at once for analysis, or can be processed sequentially throughout the day.

Yet another optional feature is polishing the surface of the area around the hole. It has been found that this greatly improved suction when just barely touching the skin. In one non-limiting example, the surface surrounding the hole is polished to the point that there are no longer any visible scratches.

The anterior vaginal wall is the location most susceptible to pelvic organ prolapse (POP) compartment conditions because this is the area where increases in abdominal pressure (by coughing, straining, etc.) apply first. Generally, the top or apex of the vagina and the back wall or posterior compartment, meanwhile are more protected and therefore less subject to prolapse.

The probe has been designed to create rapid deformations within one second suction time-intervals as well as longer deformations over six seconds to reproduce straining efforts. The device can also include surface markers, which serve to measure the anterior vaginal wall's biomechanical properties at different locations and the extent of insertion of the device; firstly, around 3 cm from the vaginal entrance or introitus, corresponding to the level of the bladder neck region; secondly, at 5 cm from the introitus, corresponding to the area of the bladder base. The probe can record several measurements at the same location. Each curve is composed of measurements obtained every $\frac{1}{10}^{th}$ of a second.

It was found that the probe provides an accurate and reliable vaginal biomechanics measurement device that is urgently needed to address the growing demands in the management of POP. POP affects a large number of aging women, tends to recur over time and often requires surgical repair. The severe changes in quality of life for those afflicted demand a major improvement in the standard of care. The best tools for examination at present are qualitative, based primarily on visual inspection and finger palpation.

But these measures are suboptimal in important ways because they are: (1) subject to operator variability; (2) do not allow quantitative time series histories; and thus (3) cannot provide accurate metrics. Therefore, the "intelligent finger" of the present invention is able to provide quantitative information for tracking the intrinsic properties of, e.g., the human vaginal wall over time.

Role in diagnosis: The degree of vaginal wall tissue impairment cannot be judged at present. Clinicians have learned to distinguish well-vascularized, strong, thick tissues with deep rugae in young healthy nulliparous women from thin tissues with effaced rugae and atrophic changes, characteristic of post-menopausal women. Presently, these are purely descriptive observations and not consistent because as POP progresses, the vaginal tissue becomes even more lax and thinner. With aging, the coloration and degree of tissue elasticity can also change towards a more pale and stretchable vaginal wall, but there is no current technique to measure, and thereby diagnose, such changes over time from the same area of the vaginal wall.

Role in surgical treatments: The present invention can also be used to reduce the risks of serious complications from trans-vaginal mesh usage for POP repair, because it can be used to test important vaginal wall tissue properties. The present invention can be used to: (1) match mesh biomechanical properties to natural vaginal wall tissue properties, in order to guide improved surgical mesh design; (2) determine suitable candidates for mesh interposition when the vaginal wall exhibits very lax parameters; (3) follow remodeling of tissue changes over time; and (4) assess the quality of surgical healing.

Role in non-surgical treatments: Pelvic floor therapy as well as local vaginal wall therapy using hormonotherapy or laser vaginal rejuvenation techniques will benefit from a direct measurement to assess progress in vaginal wall tone and elasticity. The present invention can also be used to determine if the proposed intervention has reached its goal. Nomograms of the vaginal wall tissue's intrinsic properties can be provided using the present invention to determine the range of normalcy with aging changes. The present invention can be used to determine if the abnormal tissues have returned to a normal range as would be expected if the intervention was successful. The present invention can be used for long-term monitoring of the intervention's results.

Role in prevention: Existing literature suggests a strong relationship between pregnancy and/or delivery mode (vaginal versus C-section), and the occurrence of POP later on in life. Using the present invention the user is able to measure from early on these intrinsic changes that arise when damage is detected in the post-partum phase. Thus, the present invention can be used to assess the status of the tissue to more specifically guide one or several interventions to consolidate existing tissues found to have incurred early damage, including: (1) straining prevention (avoiding heavy lifting, avoiding straining from constipation, maintaining proper body weight, tailoring sport activities to condition, treating coughing conditions, avoiding smoking); (2) hormonal supplementation when indicated, and (3) pelvic floor reeducation programs. The present invention can also be used for tracking the stabilization of early damage using bioabsorbable agents for pelvic tears, and for culturing and directly re-injecting vaginal smooth muscle cells for vaginal wall tone improvement.

There are also populations at risk of POP, based either on race or on familial pre-disposition. These women's conditions have not been well characterized in the past due to the lack of a quantitative and qualitative tool to measure their vaginal wall tissue properties. The present invention provides a simple and non-invasive measurement device that can be part of the early stages of examination of young women post-puberty to determine their vulnerability to developing POP later on in life.

Pelvic organ prolapse affects millions of women worldwide and many will need surgical repair of their vaginal wall hernias. The present invention allows for the first time a direct, rapid, simple, painless, and reproducible, office-based quantification of biomechanical vaginal wall tissue properties. These intrinsic changes will be measurable not only over time for preemptive approaches in at-risk populations, but also when damage is suspected post-partum or when guidance is needed for repair procedures later on in life to restore quality of life.

The applications for use of the present invention include, but are not limited to the following:

1. Arrays of vacuum chamber orifice-detector combinations to map vaginal wall properties simultaneously at multiple sites.

2. Substitution of a micro camera for a deflection detector in order to image the shape change of the tissue as it protrudes from the orifice into the vacuum chamber. This enables measurement of the biomechanical anisotropy of the wall tissue.

3. The parameters extracted from measurement sets such as described in items 1 and 2 enable detailed finite element biomechanical models of the tissue to be developed. These can be employed for several purposes, including: assessment of organ deformation under load; matching the compliance of a surgical mesh to that of the vaginal wall in order to enhance healing; prediction of the effects of remote perturbations of the pelvic organs (abdominal pressure, pelvic bending and twisting) on the vaginal configuration.

4. With interposition at the vacuum chamber orifice of a suitably flaccid membrane, measurement of the rheological properties of fluids entering the vaginal chamber (blood, mucus, sperm).

5. Adaptation of the probe to biomechanical measurements of normal and lesion-rich regions of the mouth (cheek, tongue, gingiva).

6. Adaptation of the probe to biomechanical measurements in the rectum (assessment of fecal incontinence, rectal tumors, polyps).

7. Adaptation of the probe to biomechanical measurements in the airway (trachea, etc.)

8. With interposition at the vacuum chamber orifice of a suitably flaccid membrane, in situ measurement of the biomechanical properties of airway mucus.

9. Adaptation of the probe to biomechanical measurements in the esophagus.

10. With interposition at the vacuum chamber orifice of a suitably flaccid membrane, in situ measurement of the biomechanical properties of fluids lining the esophagus.

11. Adaptation of the probe to biomechanical measurements in the bladder, including bladder wall compliance and degree of detrusor muscle wall aging.

12. Adaptation of the probe for minimally invasive biomechanical measurements of internal organs, including haptic assessment of tumors, etc., during the course of various surgical procedures. In this case the range of sites is limited only by the access afforded by minimally invasive catheters and the like.

In addition it was found that the present invention has additional advantages, namely: the probe of the present invention is small enough (size of a finger) that it does not require a speculum for insertion. The only variable is the skin movement. For each test, the vacuum pressure is generally always the same value and the vacuum duration is always the same as well. The infrared (IR) detector is located under the opening or aperture at the tip of the probe to directly measure the movement of the skin. The sync feature assures that the probe is placed properly and at the same pressure against the skin in order to standardize every test performed on the patient now and in the future. Too much pressure against the skin will stretch the skin and would skew the results. Good measurement reproducibility is a strength of the device of the present invention. The graphs are instantly displayed in real time and are a direct representation of skin movement. The present inventors have observed that the vaginal skin moves differently as it relaxes from the instant drop in vacuum pressure. The probe is ultrasensitive and can detect skin rebounds past zero (like a rubber band) once the pressure drops. The present invention can detect these minute variations. Furthermore, the present invention is sufficiently simple to be able to use a simple MCU (micro control unit) processor, as such; a complete computer is not a requirement to perform the test, which lowers the cost. The length of the device permits measurements at different locations along the vaginal wall or in other body orifices. The device can also be held by a tripod to avoid manual interference with the measurements, thus enhancing data reproducibility. Finally, the device can be calibrated to ensure reliable measurements over time.

Thus, the present invention provides a contactless or touchless apparatus and method for measuring skin elasticity both inside and outside the opening of the probe, and without placing any device or other item on the surface of the skin. With regard to the skin that is being tested, the present invention can use infrared, optical, or ultrasound proximity sensors to measure the proximity of the skin to the proximity sensor and is considered contactless or touchless with regard to the actual skin being tested. The raised portion improves contact with the skin that surrounds the specific location of skin that is being tested, but the present invention does not use any devices or other material (e.g., a conductive material) on the skin and underlying tissue being tested. Further, the present invention is able to measure the elasticity of the skin during one or more complete cycles, each cycle including the amount of skin drawn into the opening as a vacuum is pulled in the probe, the extent and speed with which the skin pulls out of the opening once the vacuum is withdrawn, and the extent to which the amount of skin rebounds into and from the level surface of the skin. It is important that the proximity sensor not come in contact with the skin, or with an item on the skin, so that the sensor can have a long life, but also does not affect the underlying condition of the skin being tested.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A device for measuring skin elasticity comprising:
   a probe, wherein the probe comprises one or more holes, a vacuum source, a pressure sensor, a vacuum release valve, and one or more proximity sensors aligned about the one or more holes, wherein the probe further comprises a raised area surrounding the one or more holes;
   a processor for recording the deformation of the skin using a control unit comprising a microcontroller connected to the one or more proximity sensors and the one or more pressure sensors, wherein the proximity sensor is positioned at a pre-determined distance from the skin, wherein the vacuum source is capable of increasing a vacuum from 0 to 150 mm Hg over 6 seconds, and the vacuum release valve opens to atmospheric pressure, wherein a surface of skin is defined as reference point zero, wherein the processor calculates the skin elasticity based on the distance to the one or more proximity sensors throughout a measurement cycle both inside and outside the probe; and
   a display that plots skin deformation across the reference point zero during a single measurement to determine viscoelastic properties of the skin.

2. The device of claim 1, wherein the raised area surrounds the hole and further comprises a polished surface that provides improved contact with the skin during operation.

3. The device of claim 2, wherein the handle is further defined as comprising a circuit board, a proximity sensor, a data cable connection, and a vacuum tube connection, and the proximity sensor is mounted on a circuit board that is within the probe and is attached to the handle.

4. The device of claim 3, wherein the proximity sensor is configured to measure a distance as the skin recoils when the vacuum is released, wherein the distance to the skin is measured both inside and outside the opening and the probe.

5. The device of claim 3, wherein the device is adapted to measure biomechanical measurements of normal and lesion-rich regions of the skin of the mouth (cheek, tongue, gingiva); rectum (assessment of fecal incontinence, rectal tumors, polyps); airway (trachea); or gastrointestinal tract (esophagus, stomach, duodenum, small intestine, large intestine); cardiovascular (heart, arteries or veins); or bladder (bladder wall compliance and degree of detrusor muscle wall aging), and is adapted for deployment via a catheter.

6. The device of claim 1, wherein the device further comprises a vacuum release line in fluid communication with the one or more holes of the probe to provide fresh air to refill the probe after a test under vacuum.

7. The device of claim 1, wherein the device further comprises an accelerometer or gyroscope that measures the relative angle of the probe between a vertical and horizontal position.

8. The device of claim 1, wherein the control unit further comprises a switch, an electronic control valve, and a liquid crystal display, and wherein a wand assembly is defined further as comprising a detachable handle and the probe, wherein the control unit records and stores a vacuum data and a proximity sensor data used to calculate the skin elasticity, and a memory connected to the processor to store data from the proximity sensor for immediate processing or processing at a later time.

9. The device of claim 1, wherein the proximity sensor comprises an infrared or optical sensor capable of detecting an extent and a shape of skin deflection over time without contacting the skin being measured.

10. The device of claim 1, wherein the probe further comprises at least one orifice that comprises a membrane to determine the rheological properties of a liquid on or about the skin.

11. The device of claim 1, wherein the probe further comprises one or more optic fibers between the opening and the proximity sensor, which proximity sensor is in a handle that comprises the control unit and power supply.

12. A device for measuring skin elasticity comprising:
   a probe comprising one or more holes, a vacuum source, a pressure sensor, a vacuum release valve, and one or more infrared or optical proximity sensors aligned about the one or more holes, wherein the probe further comprises a raised area surrounding the one or more holes;
   a processor for recording the deformation of the skin using a control unit comprising a microcontroller connected to the one or more infrared or optical proximity sensors and the one or more pressure sensors, wherein the one or more infrared or optical proximity sensors are positioned at a pre-determined distance from the skin, wherein the vacuum source is capable of increasing a vacuum from 0 to 150 mm of Hg over 6 seconds, and the vacuum release valve opens to atmospheric pressure, wherein a surface of the skin is defined as reference point zero, during and after release of the vacuum, and wherein the processor calculates the skin elasticity of the skin based on the distance to the one or more proximity sensors throughout a measurement cycle both inside and outside the probe; and a display that plots skin deformation across the reference point zero during a single measurement to determine viscoelastic properties of the skin.

* * * * *